US011244755B1

(12) United States Patent
Syeda-Mahmood et al.

(10) Patent No.: US 11,244,755 B1
(45) Date of Patent: Feb. 8, 2022

(54) AUTOMATIC GENERATION OF MEDICAL IMAGING REPORTS BASED ON FINE GRAINED FINDING LABELS

(71) Applicant: International Business Machines Corporation, Armonk, NY (US)

(72) Inventors: Tanveer Syeda-Mahmood, Cupertino, CA (US); Chun Lok Wong, San Jose, CA (US); Joy Tzung-yu Wu, San Jose, CA (US); Yaniv Gur, San Jose, CA (US); Anup Pillai, San Jose, CA (US); Ashutosh Jadhav, San Jose, CA (US); Satyananda Kashyap, San Jose, CA (US); Mehdi Moradi, San Jose, CA (US); Alexandros Karargyris, San Jose, CA (US); Hongzhi Wang, Santa Bruno, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 17/061,669

(22) Filed: Oct. 2, 2020

(51) Int. Cl.
*G06K 9/00* (2006.01)
*G16H 30/40* (2018.01)
(Continued)

(52) U.S. Cl.
CPC ............. *G16H 30/40* (2018.01); *G06F 40/40* (2020.01); *G06N 3/08* (2013.01); *G06T 7/0014* (2013.01);
(Continued)

(58) Field of Classification Search
CPC .......... G16H 30/40; G06F 40/40; G06N 3/08; G06T 7/0014; G06T 2207/20081; G06T 2207/30004
See application file for complete search history.

(56) References Cited

U.S. PATENT DOCUMENTS

2003/0144886 A1    7/2003   Taira
2013/0226841 A1    8/2013   Syeda-Mahmood et al.
(Continued)

FOREIGN PATENT DOCUMENTS

CN        111243729 A        6/2020

OTHER PUBLICATIONS

List of IBM Patents or Patent Applications Treated as Related, May 5, 2021, 2 pages.
(Continued)

*Primary Examiner* — Xin Jia
(74) *Attorney, Agent, or Firm* — Stephen J. Walder Jr.; William J. Stock

(57) ABSTRACT

Mechanisms are provided to implement an automated medical imaging report generator which receives an input medical image and inputs the input medical image into a machine learning (ML) computer model trained to predict finding labels based on patterns of image features extracted from the medical image. The ML computer model generates a prediction of a finding label applicable to the input medical image in terms of a finding label prediction output vector. Based on the finding label prediction output vector, a lookup operation is performed, in a medical report database of previously processed medical imaging report data structures, to find a matching medical imaging report data structure corresponding to the finding label. An output medical imaging report is generated for the input medical image based on natural language content of the matching medical imaging report data structure.

20 Claims, 16 Drawing Sheets

(51) Int. Cl.
*G06T 7/00* (2017.01)
*G06N 3/08* (2006.01)
*G06F 40/40* (2020.01)

(52) U.S. Cl.
CPC .............. *G06T 2207/20081* (2013.01); *G06T 2207/30004* (2013.01)

(56) References Cited

U.S. PATENT DOCUMENTS

| | | | |
|---|---|---|---|
| 2019/0188848 | A1 | 6/2019 | Madani et al. |
| 2019/0192096 | A1* | 6/2019 | Wu ....................... A61B 5/7267 |
| 2020/0093455 | A1 | 3/2020 | Wang et al. |
| 2020/0211692 | A1* | 7/2020 | Kalafut ................. G06T 7/0012 |
| 2020/0311861 | A1 | 10/2020 | Katouzian et al. |
| 2021/0090694 | A1* | 3/2021 | Colley ................... G16H 50/70 |
| 2021/0177522 | A1* | 6/2021 | Boddington ........... A61B 34/30 |
| 2021/0233645 | A1* | 7/2021 | Morard ................ G06K 9/6202 |

OTHER PUBLICATIONS

Abbas, Asim et al., "Meaningful Information Extraction from Unstructured Clinical Documents", Proceedings of the APAN—Research Workshop 2019, Jul. 22-26, 2019, 6 pages.

Boag, William et al., "Baselines for Chest X-Ray Report Generation", Proceedings of Machine Learning Research 116: 126-140, 2020 Machines Learning for Health (ML4H) at NeurIPS 2019, Dec. 8-14, 2019, 15 pages.

Coden, Anni et al., "SPOT the drug! An unsupervised pattern matching method to extract drug names from very large clinical corpora", 2012 IEEE Second Conference on Healthcare Informatics, Imaging and Systems Biology, Sep. 27, 2012, 7 pages.

Demner-Fushman, Dina et al., "Preparing a collection of radiology examinations for distribution and retrieval", Journal of American Medical Informatics Association, vol. 23, No. 2, Jul. 2015, 8 pages.

Goff, Daniel J. et al., "Automated Radiology Report Summarization Using an Open-Source Natural Language Processing Pipeline", J Digit Imaging (2018), 31, 185-192, published online Oct. 30, 2017, 8 pages.

Guo, Yufan et al., "Efficient Clinical Concept Extraction in Electronic Medical Records", Proceedings of the Thirty-First AAAI Conference on Artificial Intelligence (AAAI-17), Feb. 4-9, 2017, 2 pages.

Hansell, David M et al., "Fleischner Society: Glossary of Terms for Thoracic Imaging", Radiology, vol. 246; No. 3, Mar. 2008, 26 pages.

Hassanpour, Saeed et al., "Information extraction from multi-institutional radiology reports", Published in final edited form as Artif Intell Med. Jan. 2016; submitted copy Artif Intell Med. Author manuscript; available in PMC Jan. 9, 2017, 32 pages.

He, Kaiming et al., "Deep Residual Learning for Image Recognition", CVPR 2016, Conference on Computer Vision and Pattern Recognition, Jun. 26, 2016-Jul. 1, 2016, 9 pages.

He, Kaiming et al., "Identity Mappings in Deep Residual Networks", European Conference on Computer Vision, LNCS, vol. 9908, 2016, submitted version arXiv:1603.05027v3 [cs.CV], Jul. 25, 2016, 15 pages.

Irvin, Jeremy et al., "CheXpert: A Large Chest Radiograph Dataset with Uncertainty Labels and Expert Comparison", arXiv:1901.07031v1 [cs.CV], Jan. 21, 2019, 9 pages.

Johnson, Alistair E. et al., "MIMIC-CXR: A Large Publicly Available Database of Labeled Chest Radiographs", arXiv:1901.07042v1 [cs.CV], Jan. 21, 2019, 6 pages.

Karargyris, Alexandros et al., "Age prediction using a large chest X-ray dataset", SPIE Medical Imaging 2019, Feb. 16-21, 2019, 9 pages.

Karargyris, Alexandros et al., "Boosting the Rule-Out Accuracy of Deep Disease Detection Using Class Weight Modifiers", 2019 IEEE International Symposium on Biomedical Imaging (ISBI), Apr. 8-11, 2019, submitted version arXiv:1906.09354v1 [eess.IV], Jun. 21, 2019, 5 pages.

Kashyap, Satyananda et al., "Artificial Intelligence for Point of Care Radiograph Quality Assessment", SPIE Medical Imaging, 2019, Feb. 2019, 8 pages.

Kashyap, Satyananda et al., "Looking in the Right Place for Anomalies: Explainable AI Through Automatic Location Learning", 2020 International Symposium on Biomedical Imaging (ISBI), Apr. 3-7, 2020, submitted version arXiv:2008.00363v1 [cs.CV] Aug. 2, 2020, 6 pages.

Katouzian, Amin et al., "Hashing-Based Atlas Ranking and Selection for Multiple-Atlas Segmentation", International Conference on Medical Image Computing and Computer Assisted Intervention (MICCAI 2018), Sep. 16-20, 2018, 9 pages.

Laserson, Jonathan et al., "TextRay: Mining Clinical Reports to Gain a Broad Understanding of Chest X-rays", International Conference on Medical Image Computing and Computer-Assisted Intervention, Sep. 16, 2018, submitted version arXiv:1806:02121v1 [cs.CV], Jun. 6, 2018, 13 pages.

Lin, Tsung-Yi et al., "Feature Pyramid Networks for Object Detection", IEEE Conference on Computer Vision and Pattern Recognition (CVPR), Jul. 21-26, 2017, 9 pages.

Litjens, Geert et al., "A survey on deep learning in medical image analysis", Elsevier, Medical Image Analysis, vol. 42:60-88, Dec. 1, 2017, 29 pages.

Liu, Guanxiong et al., "Clinically Accurate Chest X-Ray Report Generation", Proceedings of the 4th Machine Learning for Healthcare Conference, PMLR, vol. 106, pp. 249-269, Oct. 2019, 20 pages.

McCord, M.C. et al., "Deep parsing in Watson", IBM J. Res. & Dev. vol. 56 No. 3/4 Paper 3, May/Jul. 2012, pp. 3:1-3:15.

Monshi, Maram Mahmoud A. et al., "Deep learning in generating radiology reports: A survey", Artificial Intelligence in Medicine 106 (2020) 10878, May 10, 2020, 13 pages.

Moradi, Mehdi et al., "Bimodal network architectures for automatic generation of image annotation from text", International Conference on Medical Image Computing and Computer Assisted Intervention (MICCAI 2018), Sep. 16-20, 2018, submitted version arXiv:1809.01610v1 [cs.CV], Sep. 5, 2018, 8 pages.

Nguyen, Long D. et al., "Deep CNNs for microscopic image classification by exploiting tranfer learning and feature concatenation", IEEE International Symposium on Circuits and Systems, May 2018, 6 pages.

Rajpurkar, Pranav et al., "CheXNet: Radiologist-Level Pneumonia Detection on Chest X-Rays with Deep Learning", arXiv:1711.05225v1[cs.CV], Nov. 14, 2017, 7 pages.

Simonyan, Karen et al., "Very Deep Convolutional Networks for Large-Scale Image Recognition", arXiv:1409.1556v1 [cs.CV], Sep. 4, 2014, 10 pages.

Subramanian, Vaishnavi et al., "Automated Detection and Type Classification of Central Venous Catheters in Chest X-rays", International Conference on Medical Image Computing and Computer Assisted Intervention (MICCAI 2019), Oct. 13-17, 2019, submitted version arXiv:1907.01656v3 [eess.IV], Jul. 25, 2019, 9 pages.

Syeda-Mahmood, Tanveer, Pending U.S. Appl. No. 17/061,628, filed Oct. 2, 2020, 86 pages.

Syeda-Mahmood, Tanveer et al., "Building a Benchmark Dataset and Classifiers for Sentence-Level Findings in AP Chest X-Rays", 2019 IEEE 16th International Symposium on Biomedical Imaging (ISBI 2019), Apr. 8-11, 2019, 5 pages.

Syeda-Mahmood, Tanveer et al., "Chest X-ray Report Generation through Fine-Grained Label Learning", International Conference on Medical Image Computing and Computer Assisted Intervention (MICCAI 2020), Oct. 4-8, 2020, submitted version arXiv:2007.13831v1 [cs.CV], Jul. 27, 2020, 11 pages. *[Grace Period Disclosure] *.

Syeda-Mahmood, Tanveer, "Role of Big Data and Machine Learning in Diagnostic Decision Support in Radiology", Journal of the American College of Radiology, 15(3), Mar. 2018, 8 pages.

(56) References Cited

OTHER PUBLICATIONS

Wang, Hongzhi et al., "Atlas Propagation Through Template Selection", International Conference on Medical Image Computing and Computer Assisted Intervention (MICCAI 2018), Sep. 16-20, 2018, 8 pages.

Wang, Xiaosong et al., "ChestX-ray8: Hospital-scale Chest X-ray Database and Benchmarks on Weakly-Supervised Classification and Localization of Common Thorax Diseases", 2017 IEEE Conference on Computer Vision and Pattern Recognition (CVPR), Jul. 2017, 10 pages.

Wong, Ken C. et al., "3D Segmentation with Exponential Logarithmic Loss for Highly Unbalanced Object Sizes", International Conference on Medical Image Computing and Computer Assisted Intervention (MICCAI 2018), Sep. 16-20, 2018, submitted version arXiv:1809.00076v2 [cs.CV], Sep. 24, 2018, 9 pages.

Wong, Ken C. et al., "A Robust Network Architecture to Detect Normal Chest X-Ray Radiographs", 2020 International Symposium on Biomedical Imaging (ISBI), Apr. 3-7, 2020, submitted version arXiv:2004.06147v1 [eess.IV], Apr. 13, 2020, 5 pages.

Wong, Ken C. et al., "SegNAS3D: Network Architecture Search with Derivative-Free Global Optimization for 3D Image Segmentation", Medical Image Computing and Computer Assisted Intervention (MICCAI 2019), Oct. 13-17, 2019, submitted version arXiv:1909.05962v1 [eess.IV], Sep. 12, 2019, 9 pages.

Wu, Joy et al., "Automatic Bounding Box Annotation of Chest X-Ray Data for Localization of Abnormalities", 2020 IEEE 17th International Symposium on Biomedical Imaging (ISBI), Apr. 3-7, 2020, 5 pages.

Wu, Joy T. et al., "Comparison of Chest Radiograph Interpretations by Artificial Intelligence Algorithm vs Radiology Residents", JAMA Network Open, Oct. 9, 2020, 14 pages.

Yu, Fisher et al., "Multi-Scale Context Aggregation by Dilated Convolutions", arXiv:1511.07122v1 [cs.CV], Nov. 23, 2015, 9 pages.

Yu, Kaicheng et al., "Statistically-motivated Second-order Pooling", European Conference on Computer Vision (ECCV) 2018, Sep. 8-14, 2018, 17 pages.

List of IBM Patents or Patent Applications Treated as Related, Nov. 8, 2021, 2 pages.

Bar, Yaniv et al., "Chest pathology detection using deep learning with non-medical training", 2015 IEEE 12th International Symposium on Biomedical Imaging (ISBI), pp. 294-297, Apr. 16-19, 2015, 4 pages.

Hashmi, Mohammad F. et al., "Efficient Pneumonia Detection in Chest Xray Images Using Deep Transfer Learning", Diagnostics 2020, 10, 417, Jun. 19, 2020, 23 pages.

Jadhav, Ashutosh et al., Pending U.S. Appl. No. 17/515,689, filed Nov. 1, 2021, 104 pages.

Jadhav, Ashutosh et al., "Combining Deep Learning and Knowledge-driven Reasoning for Chest X-Ray Findings Detection", AMIA Annual Symposium Proceedings, pp. 593-601; Symposium Date: Nov. 14-18, 2020, 9 pages. *[Grace Period Disclosure for U.S. Appl. No. 17/515,689]*.

Jadhav, Ashutosh, "Knowledge-driven Approach to Boost Performance of Solely Image-based Deep Learning Models", SIIM19 (Society for Imaging Informatics in Medicine) Annual Meeting, Denver, Colorado, Jun. 26-28, 2019, 2 pages.

Syeda-Mahmood, Tanveer et al., "Extracting and Learning Fine-Grained Labels from Chest Radiographs", AMIA Annu Symp Proc., pp. 1190-1199; Symposium Date: Nov. 14-18, 2020, 10 pages.

Yao, Li et al., "Learning to Diagnose from Scratch by Exploiting Dependencies Among Labels", Submitted on Oct. 28, 2017 (v1), last revised Feb. 1, 2018 (this version, v2)], https://arxiv.org/abs/1710.10501, 12 pages.

\* cited by examiner

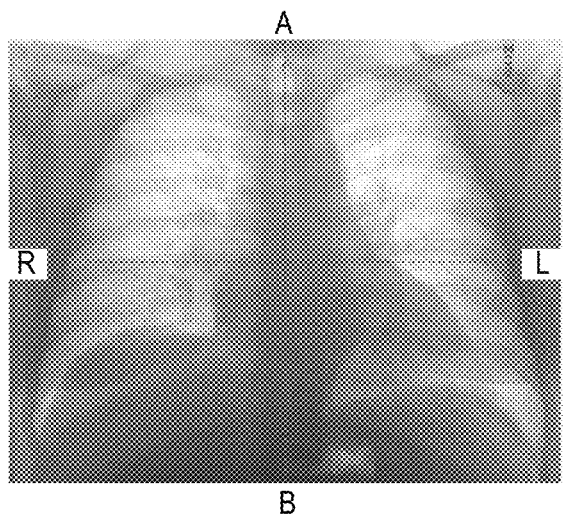
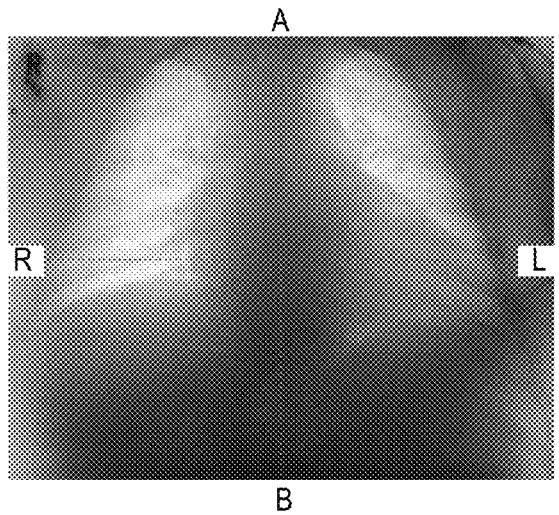

| Sample Report |
|---|
| Indications:<br>　　Rule out pneumonia and pneumothorax.<br>　　Assess for central line placement.<br><br>Findings:<br>　　Patient has been extubated.<br>　　Right IJ line tip at brachiocephalic junction.<br>　　No ptx.<br>　　No change in pleural effusion.<br>　　There is a right basilar air space opacity.<br><br>Impression:<br><br>　　Right lower lobe consolidation consistent with pneumonia.<br>　　Consider advancing central line for optimal placement. |

*FIG. 1C*

| Finding Type | Allowed Modifiers for fine-grained labels |
|---|---|
| Anatomical Finding | Anatomicalfinding\|present(positive)/absent(negative)\|corefinding\|anatomyaffected\|subanatomy\|location\|laterality\|severity\|size\|hedge\|character\|procedure\|shape\|correlation\|measure\|casue\|symptom |
| Disease | Disease\|present(positive)/absent(negative)\|corefinding\|anatomyaffected\|subanatomy\|location\|laterality\|size\|hedge\|character\|procedure\|shape\|correlation\|measure\|cause\|symptom |
| Devices | Device\|present(positive)/absent(negative)\|corefinding\|anatomyaffected\|subanatomy\|location\|laterality\|severity\|size\|hedge\|character\|procedure\|shape\|correlation\|measure\|cause\|symptom |
| Tubes and Lines | Tubesandlines\|present(positive)absent(negative)\|corefinding\|tubesandlines\|subanatomy\|tubesandlineslocation\|laterality\|severity\|size\|hedge\|character\|procedure\|shape\|correlation\|measure\|cause\|symptom |
| Tubes and Lines Finding | Tubesandlinesfinding\|ill-placed(positive)/well-placed(negative)\|corefinding\|anatomyaffected\|subanatomy\|tubesandlineslocation\|laterality\|severity\|size\|hedge\|character\|procedure\|shape\|correlation\|measure\|cause\|symptom |
| Viewpoint | Views\|positive\|findingname |

FIG. 2

| Signs and symptoms | Acquired abnormality | Anatomical |
|---|---|---|
| Congenital abnormality | Disease or syndrome | Injury or poisoning |
| Neoplastic process | Anatomical structure | Body location |
| Body part, organ, or organ component | Body space or junction | Body system |
| Fully formed anatomical structure | Therapeutic or preventive procedure | Diagnostic procedure |

FIG. 3

| Category | Finding | Category | Finding |
|---|---|---|---|
| Anatomical finding | Azygous Fissure | Anatomical finding | Lobectomy |
| Anatomical finding | Bone lesion | Anatomical finding | Lymph node calcification |
| Anatomical finding | Bullets & foreign bodies | Anatomical finding | Mass/nodule (not otherwise specified) |
| Anatomical finding | Calcified nodule | Device | Cardiac pacer and wires |
| ... | ... | ... | ... |
| Anatomical finding | Fracture | Technical Assessment | Apical lordotic |
| Anatomical finding | Hernia | Technical Assessment | Apices not included |
| ... | ... | ... | ... |
| Anatomical finding | Hydropneumothorax | Tubes and Lines | Central intravascular lines |
| Anatomical finding | Linear/patchy atelectasis | Tubes and Lines Findings | Coiled/kinked/fractured |
| Anatomical finding | Lobar/segmental collapse | Tubes and Lines Findings | Enteric tubes: incorrectly positioned |
| Anatomical finding | Enlarged hilum | Tubes and Lines Findings | Tubes in airway: incorrectly positioned |
| Device | Sternotomy wires | Tubes and Lines | Drain tubes |
| ... | ... | ... | ... |
| Modifiers: | | | |
| Anatomy affected, subanatomy, location laterality, severity, size, hedge, character, procedure, shape, correlation, measure, cause, symptom | | | |

*FIG. 4A*

| Name | codingSystem | categoryIDs | OrganSpecialtyModel.majorstructure | conceptIDs | Concepts | Source | Ontology |
|---|---|---|---|---|---|---|---|
| abdomen | cxr | anatomy | Other soft tissues | .2.297 | abdomen | lexicon | abdomen |
| abdominal | cxr | anatomy | Other soft tissues | .2.297 | abdomen | lexicon | abdomen |
| adrenals | cxr | anatomy | Other soft tissues | .2.297 | abdomen | lexicon | abdomen |
| antral region | cxr | anatomy | Other soft tissues | .2.297 | abdomen | lexicon | abdomen |
| antrum | cxr | anatomy | Other soft tissues | .2.297 | abdomen | lexicon | abdomen |
| ascending colon | cxr | anatomy | Other soft tissues | .2.297 | abdomen | lexicon | abdomen |
| bile ducts | cxr | anatomy | Other soft tissues | .2.297 | abdomen | lexicon | abdomen |
| biliary | cxr | anatomy | Other soft tissues | .2.297 | abdomen | lexicon | abdomen |
| biliary radicals | cxr | anatomy | Other soft tissues | .2.297 | abdomen | lexicon | abdomen |
| bowel | cxr | anatomy | Other soft tissues | .2.297 | abdomen | lexicon | abdomen |
| celiac axis | cxr | anatomy | Other soft tissues | .2.297 | abdomen | lexicon | abdomen |
| colon | cxr | anatomy | Other soft tissues | .2.297 | abdomen | lexicon | abdomen |
| colonic | cxr | anatomy | Other soft tissues | .2.297 | abdomen | lexicon | abdomen |
| ... | ... | ... | ... | ... | ... | ... | ... |

*FIG. 4B*

| Prefix String | Vocabulary Phrase | Matching sentence in a textual report |
|---|---|---|
| Aort:sclero, Aort:sten | Aortic sclerosis, Aortic Stenosis | Marked aortic sclerosis present with evidence of stenosis |
| Frac:clav | Fracture of clavicle | There is a transverse fracture of the mild left clavicle with mild superior angulation of the fracture fragment. |
| Perfor:esop | Perforation of esophagus | A contrast esophagram shows esophageal perforation of the anterior left esophagus at C4-5 with extraluminal contrast seen. |
| Edem:lower:extrem | Edema of lower extremity | EXTREMITIES: Lower extremity trace pitting edema and bilateral lower extremity toe ulceration and onychomycosis, right planar eschar. |
| Atri:dila | Atrial dilatation | Left Atrium: Left atrial size is mildly dilated. |
| Mass:left:brea | Mass in left breast | New lft breast palp mass found. |

*FIG. 5*

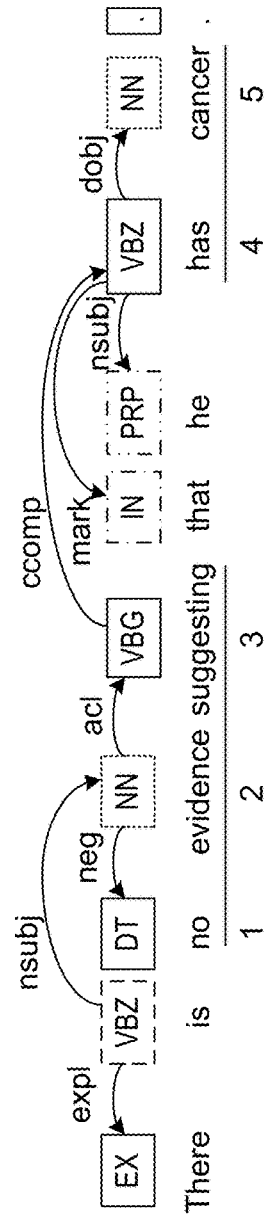

*FIG. 8*

```
findSmallestForm (word)
{
        found = false;
        i = word.length();
        prefix = word;
        while (!found && i>=3)
        {
           prefix = word.substring(0,i);
           if ((prefix not in wordMap) || (prefix not shared in wordMap))
              i--; //continue shrinking
           else
              found = true;
              prefix = word.substring(0, i+1)
        }
        return prefix;
}
```

*FIG. 6A*

```
LCF(S,T);
C[i,0] = 0, C[0,j] = 0, 0≤ i≤K, 0≤j≤N
for (1≤i≤K)
        for(1≤j≤N)
        {
          ρ_ij = |ρ_max(i,j)|/max{|s_i|, |t_j|};
          if C[i-1, j-1] + ρ_ij > C[i-1, j] && C[i-1, j-1] + ρ_ij > C[i, j-1]
                  C[i,j] = C[i-1, j-1] + ρ_ij;
          else
          {
                  If C[i-1, j] + ρ_ij > C[i, j-1]
                          C[i,j] = C[i-1, j] – δ;
                  else
                          C[i,j] = C[i, j-1] – δ;
          }
        }
```

*FIG. 6B*

```
.---------------- ndet          the1(1)                 det
.---------------- subj(n)       lung1(2,u)              noun
o---------------- top           be (3,2,5)              verb
| .-------------- vadv          normally1(4,5)          adv
`_+-------------- pred(en)      inflate2(5,u,2,u)       verb
  `-------------- vprep         without1(6,5,7)         prep
    `------------ objprep(n)    evidence1(7,u,8,u,u)    noun
      `---------- nobj(n)       of1(8,7,14)             prep
       | .------- nadj          focal1(9,u)             adj
       | | .----- nnoun         airspace1(10,u)         noun
       | | .----- nnoun         disease1(11,u,u,u)      noun
       | .-+----- lconj         pleural effusion(211)   noun
       | | | .--- nadj          pleural1(12, 13)        adj
       | | `----- chsl(n)       effusion1(13,u,u)       noun
       `-+------- objprep(n)    or1(14)                 noun
         `------- rconj         pneumothorax1(15,u)     noun
```

| Sentence | Fine-grained label | Semantics |
|---|---|---|
| There is left base streaky opacity due to xxxx scarring or discoid atelectasis | Anatomicalfinding\|yes discoid atelectasis\|\|\|\|\|\|\|\|\|discoid | Findingtype=anatomical finding<br>Core finding=discoid atelectasis<br>Positive finding? Yes<br>Shape modifier=discoid |
| There is left base streaky opacity due to xxxx scarring or discoid atelectasis | Anatomicalfinding\|yes\|streaky opacity\|base\|\|left;;base\|left\|\|or\|\|\|streaky | Findingtype=anatomical finding<br>Core finding= streaky opacity<br>Anatomy=base<br>Location=left;base | Laterality=left<br>Character=streaky<br>Positive finding? Yes |
| There is left base streaky opacity due to xxxx scarring or discoid atelectasis | Anatomicalfinding\|yes scarring | Findingtype=anatomical finding<br>Core finding=scarring<br>Positive finding? yes |
| The right upper extremity picc tip is in the upper svc. | Tubesandlinesfinding\|yes upper svc\|\|\|upper svc | Findingtype=position of tubes and lines<br>Isapositive findings? Yes<br>Corefinding=upper svc (happens to be an anatomical structure, this is a case where the core finding is the anatomy itself)<br>Location=upper svc |
| The right upper extremity picc tip is in the upper svc. | Tubesandlines\|yes picc\|extremity upper;,right upper extremity\|\|right right | Findingtype=tubes and lines<br>Positivefinding? Yes<br>Core finding=picc(line) | Subanatomy= right upper extremity<br>tubesandlineslocation=right<br>Laterality=right |

FIG. 9

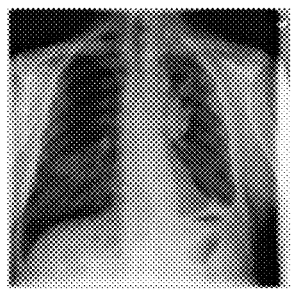 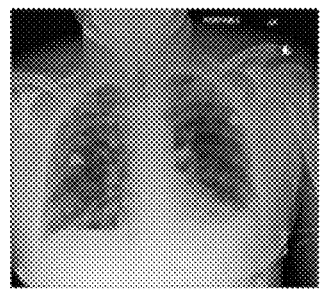 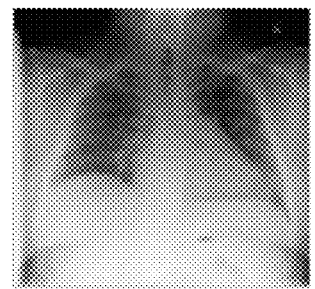

| | | |
|---|---|---|
| overall impression: Left hilar opacity may represent primary lung mass. Left hilar opacity. Left port. | Small left effusion. Pleuroparenchymal opacities at the left lung base. Wires external to patient. Surgical clips superior to the left clavical | The right hemidiaphragm is mildly elevated. Overall impression: cardiomegaly. |

GROUND TRUTH (MANUAL REPORT) 1510

| | | |
|---|---|---|
| Left perihilar opacity. Lung mass. Left port noted. | Left pleural effusion. Left lung opacities. External tubing. Surgical clips near left clavicle. | Elevated right hemidiaphragm. Enlarged cardiac silhouette. |

AUTOMATED REPORT 1520

*FIG. 15*

AUTOMATIC GENERATION OF MEDICAL IMAGING REPORTS BASED ON FINE GRAINED FINDING LABELS

STATEMENT REGARDING PRIOR DISCLOSURES BY THE INVENTOR OR A JOINT INVENTOR

The following disclosure(s) are submitted under 35 U.S.C. 102(b)(1)(A): DISCLOSURE(S): "Chest X-ray Report Generation through Fine-Grained Label Learning", Tanveer Syeda-Mahmood, Ken C. L. Wong, Yaniv Gur, Joy T. Wu, Ashutosh Jadhav, Satyananda Kashyap, Alexandros Karargyris, Anup Pillai, Aijun Sharma, Ali Bin Syed, Orest Boyko, Mehdi Moradi, arXiv:2007.13831v1 [cs.CV], Jul. 27, 2020, 11 pages.

BACKGROUND

The present application relates generally to an improved data processing apparatus and method, and more specifically to mechanisms for automatically generating medical imaging reports based on fine grained finding labels.

Leveraging machine learning capabilities of modern computing devices to assist with pattern recognition in medical image analysis is a focus of great attention in modern medical innovations. However, the quality of learning that is able to be performed by such machine learning is a function of the granularity of labels that can be attached to the medical images. Currently, only coarse-grained finding labels are able to be used with any success, making such approaches of significantly limited use in clinical practice.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided, in a data processing system specifically configured to implement an automated medical imaging report generator. The method comprises receiving, by the automated medical imaging report generator, an input medical image data structure specifying a set of image features extracted from an input medical image, and inputting, by the automated medical imaging report generator, the input medical image data structure into at least one trained machine learning computer model trained to predict finding labels based on patterns of image features extracted from medical images. The method further comprises generating, by the at least one trained machine learning computer model, a prediction of at least one finding label applicable to the input medical image based on processing the set of image features specified in the input medical image data structure and generating a finding label prediction output vector indicating one or more finding labels in a set of predefined finding labels that apply to the input medical image. The method also comprises performing, by the automated medical imaging report generator, based on the finding label prediction output vector, a lookup operation in a medical report database of previously processed medical imaging report data structures, to find a matching medical imaging report data structure corresponding to the finding label. In addition, the method comprises automatically generating, by the automated medical imaging report generator, an output medical imaging report for the input medical image based on natural language content of the matching medical imaging report data structure.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein:

FIGS. 1A and 1B are example diagrams of chest X-rays showing cardiomegaly in a patient, with FIG. 1B being a severe case;

FIG. 1C is an example medical imaging report;

FIG. 2 is a diagram showing differences in modifiers associated with different types of core findings in medical reports;

FIG. 3 is a diagram showing concept categories of UMLS relevant for finding vocabulary generation in accordance with one illustrative embodiment;

FIG. 4A is a diagram illustrating example core finding labels found by a core findings lexicon development computing tool to be sufficient for describing findings in antero-posterior (AP) chest radiographs in accordance with one illustrative embodiment;

FIG. 4B is another diagram illustrating a portion of a core findings lexicon in which the various columns of information for the core findings are shown in accordance with one illustrative embodiment;

FIG. 5 is an example diagram illustrating prefix extraction for terms within a vocabulary phrase to increase specificity of matching in accordance with one illustrative embodiment;

FIG. 6A illustrates an example of a deterministic algorithm that identifies a smallest distinguishable prefix per term in a phrase in accordance with one illustrative embodiment;

FIG. 6B illustrates an example of a longest common subfix (LCF) algorithm in accordance with one illustrative embodiment;

FIG. 8 illustrates an example of negation detection for the sentence "There is no evidence suggesting that he has cancer" in accordance with one illustrative embodiment;

FIG. 9 provides a listing of examples of types of fine-grained finding descriptors or labels extracted from sentences from redacted medical imaging reports in accordance with one illustrative embodiment;

FIG. 15 is an example diagram illustrating examples of medical imaging reports generated using manual processes versus the automated mechanisms of one illustrative embodiment.

DETAILED DESCRIPTION

Figures 7A, 7B:
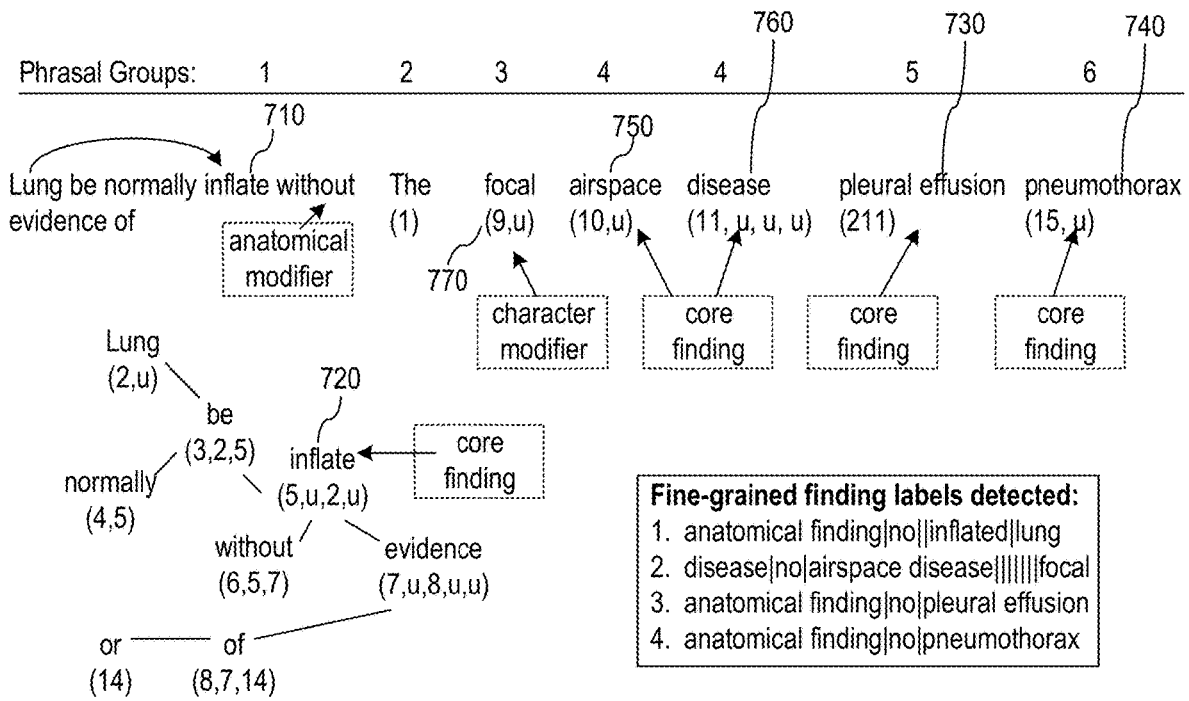
FIG. 7A illustrates a sample Slot Grammar (SG) parse tree for the sentence "The lungs are normally inflated without evidence of focal airspace disease pleural effusion or pneumothorax" in accordance with one illustrative embodiment.
FIG. 7B illustrates a depiction of a phrasal grouping process using a connected component analysis in accordance with an illustrative embodiment.

Medical imaging, such ultrasound imaging, magnetic resonance imaging, radiography, computed tomography (CT), etc., is an important part of modern medical practices, giving insights into the internal structures and medical conditions of patients that cannot be otherwise identified from outside the patient's body. However, medical imaging typically requires highly trained human beings to be able to read captured images and apply their own knowledge to what the human being sees in the images to make medical findings. This is a significant source of potential error, especially when one considers that such highly trained human beings, e.g., radiologists or the like, are increasingly being asked to read and report on larger numbers of medical imaging studies in increasingly shorter amounts of time.

To assist with these medical imaging tasks, computing tools have been developed to perform image analysis and identify coarse grained labels for medical images, such as labels identifying opacities, masses, and nodules. However, these coarse-grained labels are insufficiently described to be of use in automated medical imaging reporting. For example, using a coarse grained label of "cardiomegaly" as the label for both the images in FIGS. 1A and 1B is not sufficient to describe these images as one constitutes a severe case (FIG. 1B) and may need more prompt attention and the coarse grained label does not identify any differentiation between such cases. Before such computing tools can be incorporated into clinical practices to produce automated preliminary reads of medical imaging studies, the computing system models need to be able to recognize not only a comprehensive and broad spectrum of medical imaging findings, but also describe them in a fine grained fashion, such as covering laterality, anatomical location, severity, appearance characteristics, etc. such that distinctions between different types of the same coarse grain finding can be made apparent to the medical practitioner.

That is, a human generated full-fledged preliminary read radiology report, for example, describes various types of findings along with their positioning, laterality, severity, appearance characteristics, etc., as determined by a human being manually viewing the medical image. FIG. 1C is an example of one type of preliminary read radiology report generated manually. Currently medical image analysis computing tools are unable to provide such full-fledged preliminary reads of medical imaging studies and provide automated report generation at a same level of specificity as human generated reporting. Thus, while current medical image analysis computing tools provide some assistance to the medical practitioner, they do not have the level of detailed reporting that currently can only be achieved manually.

Thus, to capture realistic read scenarios, deep learning computer models, i.e., neural network computer models that learn through a machine learning process implemented on large sets of data, should be trained on fine-grained finding labels, where a "fine grained label" is distinguished from the "coarse grained labels" in that the fine-grained finding labels are able to differentiate different types or sub-types of findings associated with coarse grained labels by providing additional finding characteristics, such as type, positive/negative finding, and various modifiers. For example, as will be discussed hereafter, in the context of the present invention, a fine-grained label, or FFL, may be denoted by the structure $F_i=<T_i|N_i|C_i|M_i*>$ where $F_i$ is the FFL, $T_i$ is the finding type, $N_i$=yes|no indicates a positive or negative finding (i.e. is present versus absent), $C_i$ is the core finding itself, and $M_i$ are one or more of the possible finding modifiers. A coarse finding label, or CFL may include only the core finding itself without the associated attributes of finding type, positive/negative finding, and modifiers.

A number of recent approaches have attempted to take advantage of the associated medical imaging reports to automatically label the corresponding images. However, they have been limited to a small number of coarse grained core findings. Complete labeling of images for all possible findings, i.e. coarse grained core findings and more fine grained findings differentiating different types of the coarse grained core findings, seen in a specific modality of medical imaging is a challenging problem requiring the development of both vocabularies covering these findings and development of high precision and recall methods for extracting labels from the medical imaging study's associated medical imaging reports which can then be used to label the medical images for review by medical practitioners.

The illustrative embodiments provide an improved automated computer tool and computer tool methodology to automatically extract, through automated computer processes without requiring human intervention, fine-grained finding labels from medical imaging reports. The improved automated computer tool and computer tool methodology provides a comprehensive approach to extracting the fine-grained finding labels from medical imaging reports, e.g., radiology reports, which implements a new descriptor for fine-grained finding labels utilizing valid combinations of findings and their characterization modifiers, i.e. terms that characterize attributes of the findings, e.g., positioning, laterality, severity, appearance characteristics, etc., found in medical imaging reports. The illustrative embodiments further provide a vocabulary-driven concept algorithm for automatically finding these findings and modifiers from natural language content, e.g., sentences, in the medical imaging reports. The vocabulary for these findings and modifiers may be derived from established knowledge sources, such as Unified Medical Language System (UMLS) knowledge graphs, or derived from clinician curated custom lexicons. A phrasal grouping computing tool associates detailed characterization modifiers with the relevant findings in the natural language content. Positive and negative instances of a finding are separated and overall fine-grained finding labels are generated from the medical imaging report. These fine-grained finding labels may then be utilized to train a deep learning computer model, such as for labeling medical images, for example, and automatically generating preliminary read reports for medical imaging studies.

Although the primary illustrative embodiment described herein will be described with regard to generating fine-grained finding labels for training deep learning computer models to perform fine-grained finding labeling of medical images such that fine-grained findings may be automatically determined and reported from medical image processing by the trained deep learning computer model, the illustrative embodiments are not limited to such. To the contrary, the improved automated computing tool and computing tool methodology of the illustrative embodiments are applicable to other uses where it is important to have a refined understanding of the semantic context in a textual report, such as patient medical condition summary generation, for example. Moreover, being able to extract fine-grained finding label information from clinical reports, and medical imaging reports in particular, can have significant implications for clinical care, such as interpreting affected anatomy from the extracted fine grained finding label information which can trigger the scheduling of an imaging study relating to the anatomy in a downstream clinical workflow alert, using the extracted fine grained finding label identification to automatically set up reminders for appointments and trigger additional billing procedures based on the severity of the condition, etc.

Moreover, as chest radiographs, such as those shown in FIGS. 1A and 1B, are the most common diagnostic exam in emergency rooms and intensive care units today, these chest radiographs will be the example basis for explaining the improvements provided by the automated computer tool mechanisms of the illustrative embodiments. However, it should be appreciated that these are only provided as examples and the present invention may be implemented with any type of medical imaging technology currently known or later developed, in which textual reports accompany the medical images. For example, the mechanisms of the illustrative embodiments may be implemented with medical imaging studies of various technologies including, but not limited to, radiograph (e.g., X-ray radiography), computed tomography (CT), fluoroscopy, magnetic resonance imaging (MRI), medical ultrasonography or ultrasound, endoscopy, elastography, tactile imaging, thermography, medical photography and nuclear medicine functional imaging techniques, e.g., positron emission tomography (PET), and the like.

Before beginning the discussion of the various aspects of the illustrative embodiments and the improved computer operations performed by the illustrative embodiments, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on hardware to thereby configure the hardware to implement the specialized functionality of the present invention which the hardware would not otherwise be able to perform, software instructions stored on a medium such that the instructions are readily executable by hardware to thereby specifically configure the hardware to perform the recited functionality and specific computer operations described herein, a procedure or method for executing the functions, or a combination of any of the above.

The present description may make reference to "computing tools" or "tools" with corresponding functional descriptors of the computing tools, e.g., core finding lexicon development computing tool. When such terminology is used herein, the terminology is intended to refer to a specifically configured computing tool, configured with specific computing logic provided in executed software and/or hardware, to realize the function of the functional descriptor. That is, a "core finding lexicon development computing tool", for example, is a specifically configured computing tool that is specifically configured with software and/or hardware computing logic that specifically performs the operations described herein to develop a core finding lexicon. These computing tools are specialized computing tools that which are specifically configured to perform the operations to realize the corresponding function. Thus, these computing tools are not generic computing tools performing generic computer operations, but rather are specialized computing tools performing specialized functions.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As noted above, the illustrative embodiments provide a new improved automated computing tool and computing tool methodology that extracts fine-grained finding labels (FFLs) for medical images from medical imaging reports to thereby automatically learn FFLs that occur in medical imaging reports such that they can be used to train machine learning or deep learning (ML/DL) computer models that provide specialized computing tools for performing cognitive (artificial intelligence) computing operations, such as medical image labeling, automated preliminary medical imaging report generation, automated patient summary generation, or the like. The automated computing tool methodology will first be described followed by a description of the computing tool architecture. In addition, specific example embodiments of trained ML/DL models that distinguish FFLs for automated medical imaging applications and automated preliminary medical image report generation will be described.

Fine-Grained Finding Descriptor and Core Finding Vocabulary

The mechanisms of the illustrative embodiments utilize a new fine grained finding descriptor data structure to represent findings in a fine-grained manner with not only the core finding identified, but also any finding modifiers and other attributes of the finding, such as type and positivity attributes. For example, in some illustrative embodiments, the fine-grained finding descriptor data structure is defined as $F_i = <T_i|N_i|C_i|M_i^*>$ where $F_i$ is the fine-grained label, $T_i$ is the finding type, $N_i$=yes|no and indicates a positive or ruled-out finding, $C_i$ is the core finding itself, and $M_i$ are one or more of the possible finding modifiers. In this pattern, each modified $M_i$ is at its designated position separated by a |. The finding types in chest X-rays, for example, are adequately covered by six major categories namely, anatomical findings, tubes and lines and their placements, external devices, viewpoint-related issues, and implied diseases associated with findings. By analyzing a large set of chest radiology reports, the set of relevant modifiers $M_i$ for each finding type $T_i$ may be determined, and are in fact different for each finding type $T_i$, as shown in FIG. 2.

In some illustrative embodiments, in order to find a list of valid values for the core findings $C_i$ and modifiers $M_i$ for each finding type $T_i$, a semi-automated process may be implemented by a core findings lexicon development tool to perform both a top-down and bottom-up analysis of medical imaging reports and medical imaging terminology used by medical professionals, to arrive at a vocabulary or lexicon for a particular type of medical imaging, e.g., chest radiology images. The clinician-guided processes implement automated computerized natural language processing computer tools and techniques to analyze and extract features from natural language content, to perform comparisons and analysis that facilitate identifying terms or phrases, representing labels of medical image features, that are frequently used to represent medical concepts in medical image reports.

With regard to the top-down analysis, mechanisms are provided to group key visual observation labels, e.g., natural language terms or phrases, that medical imaging professionals use in medical imaging reports, into lexically and semantically meaningful groups. These groupings are then compared to a corpus of best practices literature in order to identify terms/phrases that represent core findings in each of the finding type categories. With regard to the bottom-up analysis, one or more corpora of medical imaging reports, such as may be obtained from various sources including Indiana data hub dataset, a labeled collection created from National Institutes of Health (NIH) supplied data, and the MIMIC-4 reports, are mined to extract frequently occurring n-grams, i.e. n-grams occurring more than a predetermined threshold number of times in the medical reports, that also had a mapping to categories relating the UMLS concept categories, such as those shown in FIG. 3. The frequently occurring n-grams are then queried against a clinical knowledge based providing a large dataset of medical concepts, thereby providing a set of core terms useful or findings vocabulary generation. A core term expansion tool is used to identify various forms of describing a finding (e.g., infiltrate, infiltration) or alternative ways of describing the same finding (e.g., "cardiomegaly", "heart is enlarged", "enlarged cardiac silhouette"), abbreviations, misspellings, and semantical equivalent ways of describing the same medical imaging concepts (synonyms and alternate forms), as well as ontologically related concepts.

In one illustrative embodiment, the process used to derive a list of valid values for core finding labels and modifiers for each finding type is a semi-automatic process that involves a clinician-directed curation process. Specifically, a team of clinicians (e.g., 3 radiologists and 1 internal medicine doctor) used a combination of top-down and bottom-up processes to uncover the list of findings seen in anteroposterior (AP) chest radiographs and recorded them in a chest X-ray lexicon. The clinicians systematically mapped the key visual observations (labels) that radiologists describe in the reports and grouped the labels into lexically and semantically meaningful groups based on their visual appearance similarities. Using a top-down approach, the clinicians iteratively searched through the best practices literature, including Fleishner Society guidelines, consulted several practicing radiologists, and provided a raw list of everyday use terms from their own practices to arrive at a list of core findings in each of the finding type categories. Next, using a bottom-up approach, report collections, derived from a variety of data sources including the Indiana dataset (3000 reports), internally labeled collection created from NIH supplied data (16,000 reports), and the MIMIC-4 reports (over 180,000 reports). Frequently occurring n-grams, where n varied from 1 to 13, were extracted that also had a mapping to meaningful categories related to the UMLS concept categories in FIG. 3. The resulting frequently occurring n-grams were queried against a clinical knowledge database having concepts assembled from reference vocabularies from UMLS, e.g., 70 reference vocabularies. The clinical knowledge database in one illustrative embodiment had over 5.3 million concepts. This gave rise to a set of core terms useful for findings vocabulary generation, e.g., 1500 core terms in the set of core terms. The core term expansion tool then expanded this set of core terms by capturing and relating the various forms of describing findings, alternative ways of saying the same finding, abbreviations, misspellings, synonyms, alternate forms, etc., and ontologically related concepts. Each expansion was reviewed by two radiologists for agreement resulting in a lexicon consisting of unique terms covering a space of multiple core findings and multiple modifier types, where each modifier type may have many different instances, e.g., the severity modifier may have mild, moderate, severe, chronic, acute, etc. instances. For example, as shown in FIG. 4A, in one illustrative embodiment, this lexicon consisted of over 11,000 unique terms covering the space of 78 core findings and 9 modifier types which represents the largest set of core finding labels assembled for chest radiographs to date.

The resulting core findings lexicon or vocabulary developed through an automated or semi-automated process using the core findings lexicon development computing tool provides a catalog of core finding labels along with their variants which can now be used to locate these core findings in medical imaging reports, such as radiology reports, for image labeling purposes. In one illustrative embodiment, the core finding lexicon describes the following columns: (a) the core finding term; (b) its synonyms which include alternate ways of referring to the core finding, visually similar equivalents, and spelling error variants due to spoken word translations; (c) the category of the core finding such as tubes and lines finding, devices, diseases, etc.; (d) the ontological relationship to another higher level term describing a group of core findings, e.g., fracture is an ontological group for core findings such as sternum fracture, spine fracture, etc.; (e) concept ID as an identifier to place the term in the overall lexicon; (f) the anatomical region where the finding occurs; (g) source of vocabulary (UMLS or other), (h) coding system for the concept ID (ICD9, 10 or internal coding called cxr). An example of a portion of a core finding lexicon in accordance with this illustrative embodiment is shown in FIG. 4B.

In accordance with the illustrative embodiments of the present invention, this initial core finding lexicon is used as a basis for performing fine-grained label generation. This fine-grained label generation comprises four primary operations performed by corresponding computing tools specifically configured to perform these operations. These four primary operations consist of (a) core finding and modifier detection, (b) phrasal grouping, (c) negation sense detection, and (d) fine-grained finding pattern completion.

Detecting Core Findings in Reports

With regard to detecting core findings in medical imaging reports, the illustrative embodiments use a lexicon or vocabulary driven concept extraction process to identify all occurrences of core findings and/or their synonym variants in sentences within medical imaging reports. The medical imaging reports, e.g., radiology reports, are pre-processed to isolate the sections describing the findings and impression. Often, these are indicated by section headings found in medical imaging reports and thus, the pre-processing can use natural language processing to identify section headings and the terms in such section headings that are indicative of findings or impressions. The lexicon or vocabulary driven extraction process is then executed on the identified sections of the medical imaging reports.

In order to perform the lexicon or vocabulary driven extraction process, the process first builds a vocabulary index data structure in which each synonym of the core finding points to the core finding phrase in the lexicon. This index may be built upon the core findings lexicon or vocabulary developed through the automated or semi-automated process using the core findings lexicon development computing tool discussed previously. This ensures that a match to a core finding phrase can be found through its synonyms using the vocabulary index data structure. To ensure a match to various word forms of the core finding phrases, the core finding terms are pre-processed by retaining essential prefixes of terms within a core findings prefix data structure such that the combined presence of these prefixes points to the actual core finding phrase in the vocabulary (lexicon). For example, in FIG. 5, column 510 lists the prefix strings for the core findings phrases in column 520. Matching sentences in a textual report for each of the prefix strings are shown in column 530.

The set of prefixes that best discriminate a core finding phrase (also referred to as a vocabulary phrase) can be determined by a deterministic algorithm that iteratively shortens each term in a phrase until it fails to be discriminatory in identifying the vocabulary phrase. An example of such a deterministic algorithm that identifies the smallest distinguishable prefix per term in a phrase is shown in FIG. 6A. In FIG. 6B an example of a longest common subfix (LCF) algorithm is provided, as will be discussed hereafter.

In one illustrative embodiment, the core findings lexicon or vocabulary is pre-processed by this smallest prefix building algorithm to record all prefix strings in the vocabulary index. Generation of the prefix strings is part of the preparation to put the lexicon in an index. The prefix generation process reduces the chance of false matches while increasing precision since the prefix generated is relatively unique for the vocabulary term. For detecting the vocabulary phrase, all prefix terms from vocabulary phrases are searched within the portions of natural language content, e.g., sentences, from the relevant sections of medical imaging reports, e.g., the findings and impression sections, and those vocabulary phrases with full matches to the prefixes are retained. This minimizes the false positives in matching the concepts, particularly for multi-term phrases. Once the candidate vocabulary phrases are identified, a detailed match is initiated within the portions of natural language content, e.g., sentences, in which they were found using a dynamic programming algorithm to align the words of candidate vocabulary phrases to the portion of natural language content (hereafter assumed to be sentences, but which can be any multi-term portion of natural language content) using the prefixes. The resulting alignment guarantees the largest number of words of the vocabulary phrase are matched to the largest possible extend in the sentence while still maintaining the word order and allowing missed and spurious words in between.

For example, given a query vocabulary phrase $S=<s_1 s_2 \ldots s_K>$ of K words and a candidate sentence $T=<t_1 t_2 \ldots t_N>$ of N words, a longest common subfix (LCF) is defined as $LCF(S,T)=<p_1 p_2 \ldots p_L>$, where L is the largest subset of words from S that found a partial match in T, and pi is a partial match of a word $s_i \in S$ to a word in T. A word $s_i$ in S is said to partially match a word $t_j$ in T if it shares a maximum length common prefix $p_i$ such that $$\frac{|p_i|}{\max\{|s_i|, |t_j|\}} \geq \tau,$$

where τ is a threshold such that if the threshold is set to 1.0, the evaluation reduces to a case of finding exact matches to words of S. Aligning to prefixes was selected in order to correspond to the English grammar rules where many word forms of words share common prefixes. This allows for the modeling of word variants, such as "regurgitated", "regurgitating", and "regurgitation", as they all share a sufficiently long prefix "regurgitat." The alignment to prefixes also allows for modeling spelling errors, particularly those that are made in the later portion of a word which will be deemphasized during alignment.

As noted above, an example LCF based algorithm is shown in FIG. 6B. In the depicted LCF based algorithm, $p_{max}(i, j)$ is the longest prefix of the strings $s_i t_j$ and S is a mismatch penalty, which controls the separation between matched words and prevents words that are too far apart in a sentence from being associated with the same vocabulary phrase, thus minimizing the effect of incorrect anaphora resolution in a sentence. Using such an LCF based algorithm, a vocabulary phrase S is said to be detected in a sentence T if $$\frac{|LCF(S, T)|}{|S|} \geq \Gamma$$

for a threshold $\Gamma$. The choice of $\tau$ and $\Gamma$ affect precision and recall in matching and can be suitably chosen to meet specified criteria for precision and recall based on a Receiver Operating Characteristic (ROC) curve analysis. It should be noted that the normalization in the previous equation is on the length of the vocabulary phrase and not the sentence allowing matches to be found in long sentences.

Referring again to FIG. 5, the depicted table illustrates examples of prefix extraction for terms within a vocabulary phrase to increase specificity of matching. In FIG. 5, column 520 shows the vocabulary phrases that were recognized from sentences shown in column 530. As can be seen, the LCF based algorithm, such as the one shown in FIG. 6B, is able to spot the occurrence of both "aortic sclerosis" and "aortic stenosis" in the sentence, even though the words "aortic" and "stenosis" are separated by several words in between. Similarly, the vocabulary phrase "left atrial dilatation" was matched to "Left Atrium: Left atrial size is mildly dilated" even without a deep understanding of the linguistic origins of the underlying words.

Associating Modifiers with Relevant Core Findings

The above vocabulary-driven phrasal detection algorithm can be applied to the vocabulary of both core findings and modifiers in the core findings lexicon (vocabulary) to appropriately tag phrases within sentences. The first step in fine-grained finding detection is to detect the core finding itself using the vocabulary-driven concept extraction method. This method also identifies other terms corresponding to modifiers as well, such as anatomy, location, laterality, etc. Again, during lexicon development, both core findings and modifier types, with corresponding modifier instances, are identified through the semi-automated process, which can then be used to identify phrases in natural language content having core findings and modifiers. The subsequent steps perform natural language parsing, phrasal grouping, etc. By "tagging" what is meant is the identifying of the vocabulary terms from the lexicon within the sentence and marking them as such, i.e. marking them as core finding, modifier type, etc.

To generate fine-grained finding labels (FFLs), the modifiers are associated with the relevant core findings. Doing this without full natural language understanding can be difficult. For example, in the sentence "The lungs are normally inflated without evidence of focal airspace disease, pleural effusion or pneumothorax" is the modifier "focal" associated with airspace disease only, or also with pleural effusion and pneumothorax?

The illustrative embodiments use a natural language parser, such as the English Slot Grammar (ESG) parser, for example, which performs word tokenization, sentence segmentation, morpho-lexical analysis, and syntactic analysis to produce a dependency parse tree, which in the ESG parser mechanism is called the Slot Grammar (SG) parse tree. Using ESG and the SG parse tree as an example, in the SG parse tree, each tree node N is centered on a head term, which is surrounded by its left and right modifiers, which are, in turn, tree nodes. Each modifier M of N fills a slot in N. The slot shows the grammatical role of M in N and is indicated by a tuple T=(t1, t2, . . . tk) which means that t1 is a term grammatically related to modifiers t2, . . . tk. Here, an unknown modifier is indicated by the symbol "u". A sample SG parse tree for the sentence "The lungs are normally inflated without evidence of focal airspace disease pleural effusion or pneumothorax" is shown in FIG. 7A. The association tuples are also shown in FIG. 7A, such as for the word "without", the tuple (6,5,7) indicates the word "without" is relating the term "inflate" to "evidence." Associations that logically go together, such as adjectives describing nouns, are already indicated by the ESG parser through numeric codes exceeding 100, such as for the term "pleural effusion" which has the slot structure (211) and is also seen by the pairing (12, 13).

Given such a dependency parse tree G and the tuples $T_G = \langle T_1, T_2, \ldots T_N \rangle$ corresponding to the N tree nodes, where $T_i = (t_{i1}, \ldots t_{ki})$ is the tuple per node, a phrasal group is defined as $P_1 = (e_1, e_2, \ldots e_M)$ where $e_j = t_{jk} \in T_j$ is the kth element of a tuple $T_j$ and $\forall_{j=1}^M T_j \cap T_{j+1} \neq 0$. In other words, a phrasal group is a connected component formed from the transitive closure of the tuples such that they have at least one element in common. Consider the sentence "Clear lungs without evidence of pneumonia". The natural language parser would produce a dependency parse tree like that shown in Table 1 below. In this case, it can be seen that (1,2,u) for "clear" indicates words 1 and 2 can be grouped together because they already occur in the dependency parse tree and are indicated by the parser. The word "of1" (5,4,6) is similarly indicating that words 4, 5, and 6 belong to a connected component. Now the word "evidence2" (4,2,u) can be used to infer that the words "evidence of pneumonia" can be further grouped with "lung" (which in turn can be grouped with "clear") to form a larger connected component. Thus, the cues inside the dependency parse tree are used to recursively group words or terms into larger and larger connected components. Initially each connected component may be a single word or a few words already in a relationship such as "clear1"(1,2,u), but after the grouping algorithm we get a larger group (1,2,4,5,6) all in one phrasal group or (clear, lung, evidence, of, pneumonia).

TABLE 1

Example dependency parse tree for sentence "Clear lungs without evidence of pneumonia"

| .- nadj | clear1 (1,2,u) | adj ∈ |
| .-+- subj(n) | lung1 (2,u) | noun |
| \| '- nadjp | without2 (3,u) | adv r |
| o--- top | evidence2 (4,2,u) | verb |
| '--- vprep | of1 (5,4,6) | prep |
| '- objprep(n) | pneumonia (6,u,u) | noun |

FIGS. 7A and 7B illustrate another example of the phrasal grouping process and the groups produced for the sentence shown at the top of the figure. FIG. 7A shows a dependency parse tree of the sentence "The lungs are normally inflated without evidence of focal airspace disease pleural effusion or pneumothorax" generated by an ESG parser. FIG. 7B is a depiction of a phrasal grouping process in accordance with the illustrative embodiments, using a connected component analysis. In FIG. 7B, the core findings from the core findings lexicon that occur within phrasal groups are identified as elements 710-740. Core findings that cross phrasal groups are identified as elements 750-760. The modifier is indicated as element 770. The term "Lung" in the depicted example is another indicated modifier 780 of a "anatomy" type.

Since the core findings and modifiers were detected from a prior stage of processing, i.e. the first stage of the fine-grained finding labels where detection of the vocabulary terms of the lexicon, including terms corresponding to core findings and terms corresponding to modifier types, within the natural language content, these core findings and modifiers are mapped back into the phrasal group by identifying phrasal groups that contain core findings and/or modifiers of core findings in the core findings lexicon or vocabulary. Phrasal groups that contain one or more core findings are called "core phrasal groups" or "core groups" while the rest of the groups are called the "helper phrasal groups" or "helper groups". In the depicted example, phrasal groups 1, 4, 5, and 6 are core phrasal groups whereas the other groupings are helper groups. If a core finding is detected across two or more adjacent core groups, where adjacent core groups are groups in the parse tree that have an edge that directly connects the two groups such that adjacency is based on the nearest consecutive words in the groups, then they are also merged to form a single core group as shown in FIG. 7B where the original phrasal groups for "airspace" and "disease" are combined to generate grouping 4. All modifiers present in helper groups are associated with the core findings of their adjacent groups. Thus, in FIG. 7B, the modifier "focal" in helper group 3 is associated with the core findings of the adjacent core group 4, i.e. "airspace disease". FIG. 7B also lists the various phrasal groups and the two core finding associations found in the sentence (shown as arcs).

Negated Instance Detection of Core Findings

To determine if a core finding is a positive or negative finding (e.g., "no pneumothorax"), such that the correct value for a corresponding positivity characteristic in the fine-grained label descriptor data structure may be set, a two-step process is followed that combines language structuring and vocabulary-based negation detection. The language structuring approach to negation detection starts from a dependency parse tree of a sentence. A set of known negation dependency patterns, such as may be developed by computerized natural language processing (NLP) mechanism developers, is used to search for negation keywords and the scope of words spanned by a negation keyword. The negation pattern detection algorithm iteratively identifies words within the scope of negation of a detected negation keyword based on dependency parsing and pattern matching of the predetermined negation dependency patterns. For example, let S be the set of negated words. The algorithm starts by adding a collection of manually curated negation keywords or cues (e.g., "no") into S, and then iteratively expanding S through traversing the dependency parse tree of a sentence until S becomes stable, i.e. no more words/terms are added to the set of negated words S.

FIG. 8 shows an example of negation detection for the sentence "There is no evidence suggesting that he has cancer." Based on the computerized natural language processing of the natural language content, e.g., the sentence shown in FIG. 8, and the negation pattern matching, the negation scope, i.e. the set of negated words S, is determined to be "evidence", "suggesting", "has", and "cancer", and the target vocabulary phrase is identified as "cancer."

The above described negation detection algorithm is dependent on the correctness of the dependency parse tree data structure. To ensure that the negation keywords, are being associated with the relevant core phrasal group, a vocabulary of "negation prior" and "negation post" terms is developed and utilized such that their occurrence prior or post the core finding in the natural language content is a further indication of negation or avoiding spurious negation detection. This negation prior and negation post evaluation may be performed after the language analysis of the negation detection algorithm operates on the parse tree data structure to identify patterns of negation. By explicitly looking for these negation terms indicating pre or post terms surrounding a core finding, the negation detection can have improved precision. That is, the natural language processing of the negation detection algorithm that identifies patterns within the dependency parse tree uses the dependency parse tree but does not explicitly account for the fact that it is the core finding whose negated instance that is trying to be detected. The use of the pre and post negation terms reduced the negation detection error, such as from approximately 7% to approximately 2%. The pre- and post-negation terms may be documented in the core finding lexicon. By adding the pre- and post-negation term detection mechanism to the negation detection algorithm, based on the pre and post negation terms in the core finding lexicon, performance of the negation detector was found to be improved by a significant amount.

Fine-Grained Finding Descriptor Formation

Through the above processes, core findings in portions of natural language content of medical imaging reports are identified and the phrasal groups associated with core findings are further identified so as to identify which modifiers are associated with the core findings. Whether or not a core finding is positively or negatively identified in these portions of natural language content is further determined using the extended negation detection algorithm described previously which includes both negation pattern detection and pre- and post-negation term occurrence identification. These identified characteristics of a core finding in medical imaging reports are then combined to form a fine-grained finding descriptor data structure that identifies a fine-grained finding pattern which can be used to identify similar occurrences of the fine-grained finding pattern in other medical imaging reports.

To form the fine-grained finding descriptor data structure, using the fine-grained finding descriptor format previously described above, i.e. the tuple defined as $F_j = <T_i | N_i | C_i | M_i^*>$, the fine-grained finding descriptor formation process begins with the core finding Ci and the associated modifiers Mi discovered during the phrasal grouping process discussed above. For each core finding Ci, its finding type is retrieved from the core findings lexicon or vocabulary. Further, due to the a priori knowledge captured in the core findings lexicon or vocabulary for the associated anatomical locations of findings, the fine-grained findings descriptor can be augmented with the anatomical location even when these are not specified in the natural language content of the medical imaging report itself. In addition, the name of the core finding may be ontologically rolled-up to the core findings from the core finding lexicon. That is, in the core finding lexicon, the core finding name and all of its synonyms are specified. In addition, the fine-grained finding name may be rolled-up into the core finding name. For example, if sternum fracture was a core finding in the core finding lexicon, the ontology column of the core finding lexicon will include "fracture" while the synonym column may include "sternal fracture", "sternum bone abnormality", etc. (see example in FIG. 4B as discussed previously).

The results of the extended negation detection algorithm, indicating whether or not the core finding is positively or negatively indicated in the natural language content, and thus, positively or negatively indicated by the fine-grained finding pattern defined by the fine-grained finding descriptor, may be used to set the value of the negation attribute Ni in the fine-grained finding descriptor data structure.

Thus, all of the components of the fine-grained finding descriptor data structure are provided through the processes above and used to generate the fine-grained finding descriptor data structure. This process is repeated for each core finding in each portion of natural language content processed to generate a database of fine-grained finding descriptor data structures that are found in medical imagine reports. The resulting fine-grained finding descriptor data structures may then be filtered so as to only retain a subset of fine-grained finding descriptor data structures that satisfy desired frequency thresholds. That is, a frequency threshold may be predetermined that indicates how many times a fine-grained finding descriptor data structure must be found present in medical imaging reports in order for it to be maintained in a final set of fine-grained finding descriptor data structures of the database, e.g., 100 instances.

The resulting database of fine-grained finding descriptor data structures can then be used to train machine learning computer models, such as deep learning computer models and the like, to find instances of similar fine-grain finding patterns in other natural language content. The detection of the fine-grained finding patterns defined by the fine-grained finding descriptor data structures in other natural language content may be used as a basis for performing other cognitive computing operations, such as medical image labeling or the like. For example, rather than training a machine learning computer model, deep learning computing model (neural network), or the like, to perform medical image labeling, such models, automated computing tools, or neural networks may be trained to perform other types of automated cognitive computing operations, one of which may be patient synopsis generation. With a patient synopsis embodiment, the trained machine learning computer model, deep learning computing model, or other trained computing tool takes patient electronic medical records, which may include medical imaging reports, and summarize the patient's medical condition based on the detection of fine-grained findings in the patient's electronic medical records. Such a use will present the synopsis to the medical practitioner who can then review the patient's electronic medical record with a focused approach directed to the portions associated with the patient synopsis, e.g., locating the particular medical images that would show the fine grained findings indicated in the patient synopsis, identifying the lab results that would support/refute the fine grained findings, etc.

FIG. 7B lists fine grain finding descriptors, or fine grain finding labels, extracted from the sentence shown in that figure. As can be seen, both positive and negative instances of findings have been extracted by the process of the illustrative embodiments. FIG. 9 provides a listing of examples of types of fine-grained finding descriptors or labels (FFLs) 920 extracted from sentences 910 from redacted medical imaging reports. The semantics column 930 shows the meaning of the FFL pattern shown in corresponding rows of column 920. That is, each FFL pattern in column 920 is of the form $F_i = <T_i|N_i|C_i|M_i^*>$, as described previously. Thus there is a designated position for each modifier type. From the FFL pattern extraction process, a unique FFL pattern is detected in the sentences of the natural language content of the medical imaging reports, described in the above syntax, with the semantics indicated in column 930. A label code, such as L1, may be assigned to the unique FFL pattern to designate other patterns in other natural language content that correspond to the unique FFL and which can be referred to during machine learning.

As can be seen, important details of the finding are adequately captured in the generated fine-grained finding descriptor or label (FFL) 920, despite the redaction such that the mechanisms of the illustrative embodiments may be run on redacted medical imaging reports and yet still generate a sufficiently detailed fine-grained finding descriptor or label to be used to trained machine learning computer models. In one illustrative embodiment, by mining the findings and impression sections of over 220,000 radiology reports, the above process of the illustrative embodiments was able to record all possible fine-grained finding descriptors/labels that could be extracted and then, by retaining only those fine-grained finding descriptors/labels that were found in at least 100 medical imaging reports, a total of 457 fine-grained finding labels were selected. Of these, 78 were the original core labels identified in the core finding lexicon, and the remaining were finer-grained labels with modifiers extracted automatically using the above processes. FIG. 9 provides an example of some fine-grained finding labels extracted from medical imaging reports and retained as part of a fine grained finding descriptor database using the processes of the illustrative embodiments.

Training Machine Learning Computer Models for Image Labeling

Having developed a database of fine-grained finding descriptor data structures, which define fine grained finding labels (FFLs) or descriptors, the database may be used for various downstream artificial intelligence and cognitive computing operations. These artificial intelligence and cognitive computing operations may involve trained machine learning/deep learning models or may involve other computer logic that implements complex analysis and evaluation of data structures for presentation of information otherwise not able to be easily identifiable by human users or to perform computer operations that cannot be practically performed by human beings due to various factors including, but not limited to, the volume of data being evaluated, the complexity of relationships between data that must be evaluated, or the like.

In some illustrative embodiments, the FFLs defined in the fine-grained finding descriptor data structures may be used in downstream computing systems to perform operations such as identifying an highlighting or otherwise accentuating portions of electronic medical records and/or summarizations of electronic medical records that have a matching FFL. This will provide additional focus to medical imaging subject matter experts on portions of complex electronic medical records/summarizations on the most important portions corresponding to findings which may affect a patient's diagnosis, treatment, or other understanding of the health condition of the patient. In such a downstream computing system, a machine learning model may be utilized, or may not be utilized. That is a computerized pattern matching mechanisms may be employed which does not require machine learning to operate, yet provides a complex analysis of electronic medical record content using other computer constructs, such as a rules engine or the like.

However, in other illustrative embodiments, the FFLs of the fine-grained finding descriptor data structures in the database may be implemented to train a machine learning/deep learning (ML/DL) computer model that is able to distinguish between the fine-grained finding labels. As noted above, while the illustrative embodiments may be used to train ML/DL computer models for identifying FFLs in natural language content to facilitate various types of cognitive computing operations, one principle cognitive computing operation for which such a ML/DL computer model may be trained is to perform medical image labeling, i.e. identifying structures, abnormalities, etc. associated with findings in medical images and appropriately labeling them as such. Such learning involves correlating features extracted from medical images with findings found in the natural language content of corresponding medical imaging reports such that the trained ML/DL computer model learns associations and patterns between medical image features and findings specified in the natural language content. Through training of the ML/DL computer model, these associations are learned and can be used to identify similar patterns in other inputs of medical images and/or medical imaging reports. For example, given features, e.g., an image pattern, extracted from a medical image, the trained ML/DL computer model may predict the labels for the extracted features based on the learned associations with FFLs defined by the fine-grained finding descriptor data structures. Similarly, given a medical imaging report, and identifying an instance of natural language content matching a FFL of a fine-grained finding descriptor data structure, the trained ML/DL computer model can predict the location in a medical image of a corresponding structure, abnormality, etc. based on the learned associations of the FFL of the fine-grained finding descriptor data structure with medical image features.

The learning of FFLs from chest radiographic images, for example, is a fine-grained classification problem for which single networks used for computer vision problems may not yield the best performance as large training sets are still difficult to obtain. Concatenating different image dataset pretrained features from different trained ML/DL computer models, e.g., neural networks, can improve classification. Thus, in some illustrative embodiments, pretrained features, such as ImageNet-pretrained features, from different trained ML/DL computer models for computer vision are combined through a feature pyramid network using features across multiple scales. An example of a ML/DL computer model of this type using concatenation of different image dataset pretrained features is shown in FIG. 10.

Figure 10:
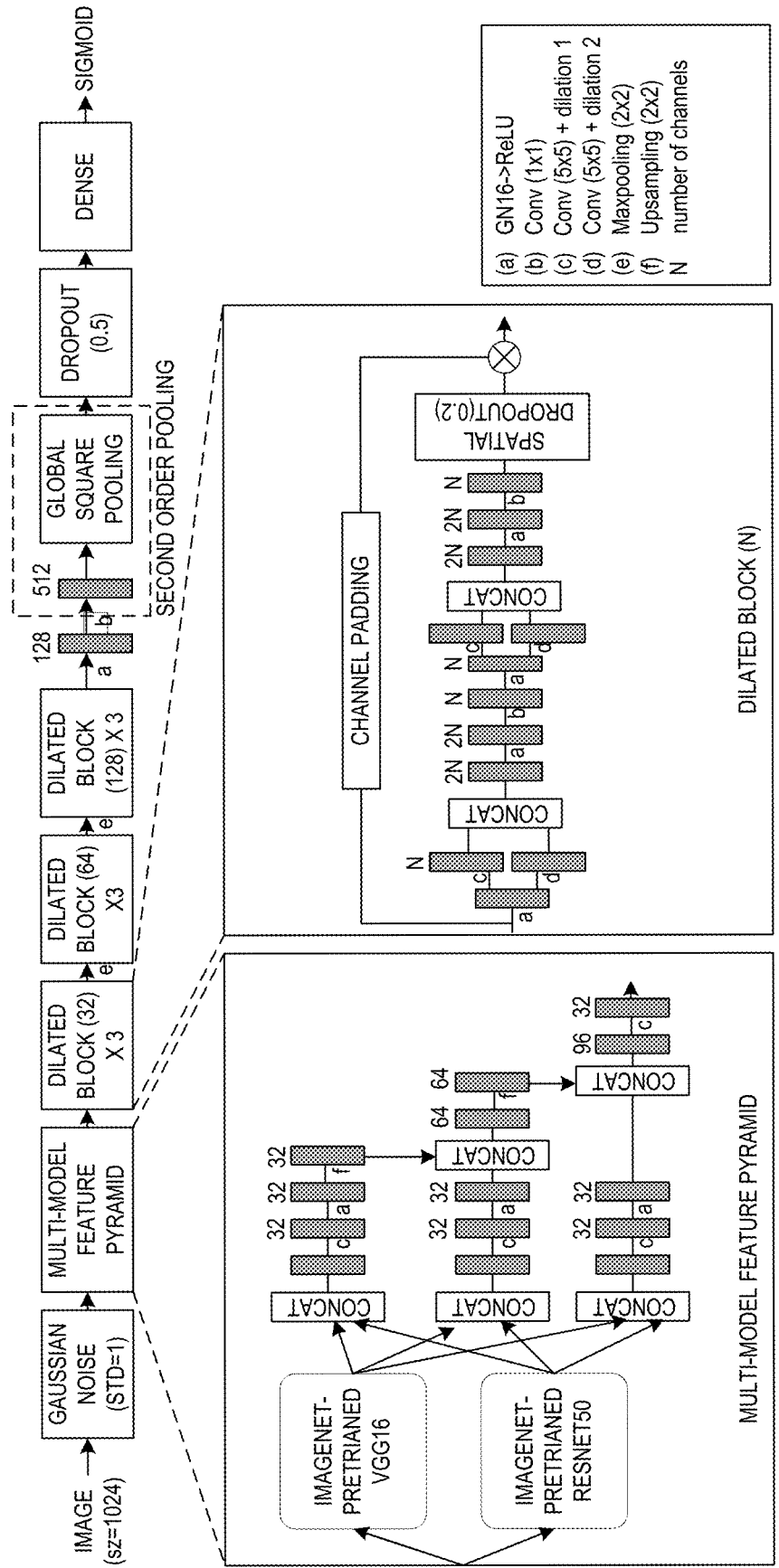
FIG. 10 is an example of a machine learning/deep learning (ML/DL) computer model that may be trained for medical image augmentation (labeling) in accordance with one illustrative embodiment.

For this example embodiment in FIG. 10, the VGGNet and ResNet are used as feature extractors and their lower-level features are retained. In particular, in one illustrative embodiment, from the VGGNet, feature maps with 128, 256, and 512 feature channels are used, which are concatenated with the feature maps from the ResNet of the same spatial sizes which have 256, 512, and 1024 feature channels. Dilated blocks are used to learn the high-level features from the extracted features, e.g., ImageNet features. Each dilated block is composed of dilated convolutions for multi-scale features, and uses a skip connection of identity mapping to improve convergence and spatial dropout to reduce overfitting. Group normalization (e.g., 16 groups) is also used with Rectified Linear Unit (ReLU). Dilated blocks with different feature channels are cascaded with max pooling to learn more abstract features.

Second-order pooling is used, which is proven to be effective for fine-grained classification and maps the features to a higher-dimensional space where they are more separable. In some illustrative embodiments, the second-order pooling is implemented as a 1×1 convolution followed by global square pooling.

Image augmentation with rigid transformations is used to avoid overfitting. As most of an image should be included, in some illustrative embodiments, the augmentation is limited to rotation (+/−10°) and shifting (+/−10°). In one illustrative embodiment, the probability of an image to be transformed is 80% and the optimizer Nadam is used with a learning rate of $2 \times 10^{-6}$, a batch size of 48, and 20 epochs. In some illustrative embodiments, such as in the illustrative embodiments described hereafter with regard to automated imaging report generation, to ensure efficient machine learning, two instances of the ML/DL computer model shown in FIG. 10 are trained, one for core finding labels (CFL labels) and the other for the detailed fine-grained finding labels (FFL labels) which have support of at least a predetermined number of images, e.g., 100 images, for training to exploit the mutually reinforcing nature of the coarse-fine labels. Due to the variability in the size of the dataset per FFL, the Area under the ROC Curve (AUC) per FFL is not always a good indicator for precision on a per image level as it is dominated by the negative examples. To ensure as few irrelevant findings as possible while still detecting critical findings within an image, operating points on a ROC curve per label are selected based on optimizing the F1 score, a well-known measure of accuracy, as $$L(\theta) = -\ln\left(\frac{1}{n}\sum_{i=1}^{n} F1_i(\theta)\right).$$

In one illustrative embodiment, a deep neural network architecture was designed that combines the advantages of pretrained features with a multi-resolution image analysis through a feature pyramid network for fine grained classification. Specifically VGGNet[21] (16 layers) and ResNet (50 layers) were used as the initial feature extractors, which were trained on multi-million images from ImageNet. Dilated blocks composed of multi-scale features and skip connections were used to improve convergence while spatial dropout was used to reduce overfitting. Group normalization (16 groups) was used, along with Rectified Linear Unit (ReLU) as activation function. Dilated blocks with different feature channels were cascaded with max pooling to learn more abstract features. Bilinear pooling was used for effective fine-grained classification.

To train the deep learning model, the modeling dataset was split into three partitions for training, validation and testing. Since existing methods of random splitting cannot ensure adequate number of images for low incidence label training, the splitting algorithm in this example embodiment sorted the labels by their frequencies of occurrences. The splitting algorithm then iteratively assigned the images from distinct patients to the three partitions in the ratio of 70-10-20% for training, validation and testing. Once the number of patients in each split was determined per label, the assignment of the patients/images was still random. Thus, the algorithm ensured that the prevalence distributions were similar for training, validation and testing partitions while minimizing the selection bias through random sampling of images.

The deep learning model was trained on all finding labels (CFLs and FFLs depending on the model trained). As the images were of high resolution (e.g., 1024×1024), training took approximately 10 days. The Nadam optimizer was used for fast convergence with the learning rate as $2\times10^{-6}$. Two NVIDIA Tesla V100 GPUs with 16 GB memory were used for multi-GPU training with a batch size of 12 and 30 epochs.

Computing Environment and Computing Architecture

The illustrative embodiments provide an improved computing tool and improved computing tool methodology to automatically learn fine-grained finding labels (FFLs) used in the natural language content of medical imaging reports and generate fine-grained finding descriptor data structures that define fine-grained finding patterns. The fine-grained finding descriptor data structures can then be used to train machine learning/deep learning (ML/DL) computer models, such as neural networks or the like, to perform artificial intelligence (cognitive computing) operations based on the detection of such fine-grained finding patterns in other natural language content, such as other medical imaging reports, other portions of patient electronic medical records, or the like. In this way, improved automated computing tools are provided to assist human medical practitioners in understanding and identifying findings in a patient's electronic medical records (EMRs), thereby improving the way that the human medical practitioner can perform their duties of providing care to their patients. That is, the improved automated computing tools are able to surface, from the large combination of medical information data of a patient's electronic medical record, the subset of information of particular importance for the medical practitioner's attention corresponding to fine-grained findings. This reduces the likelihood that the medical practitioner will miss information in the patient's EMR, or miss associations of information in the patient's EMR because this information is obscured by the complexity and/or volume of information present in the patient EMR, or the difficulty in identifying specific structures/abnormalities in medical imaging data. The improved computing tools of the illustrative embodiments automatically learn fine-grained finding patterns and automatically uses the learned fine-grained finding patterns to identify instances of such patterns in patient electronic medical records to thereby extract associated information from the patient electronic medical records and perform other artificial intelligence (cognitive computing) based operations to assist medical practitioners, such as automatically labeling structures/abnormalities in medical images, automatically generating preliminary medical imaging reports, automatically generating patient electronic medical record summaries that specify specific subsets of pertinent information extracted from the patient electronic medical record that is of particular importance to medical practitioner review, etc.

Figure 11:
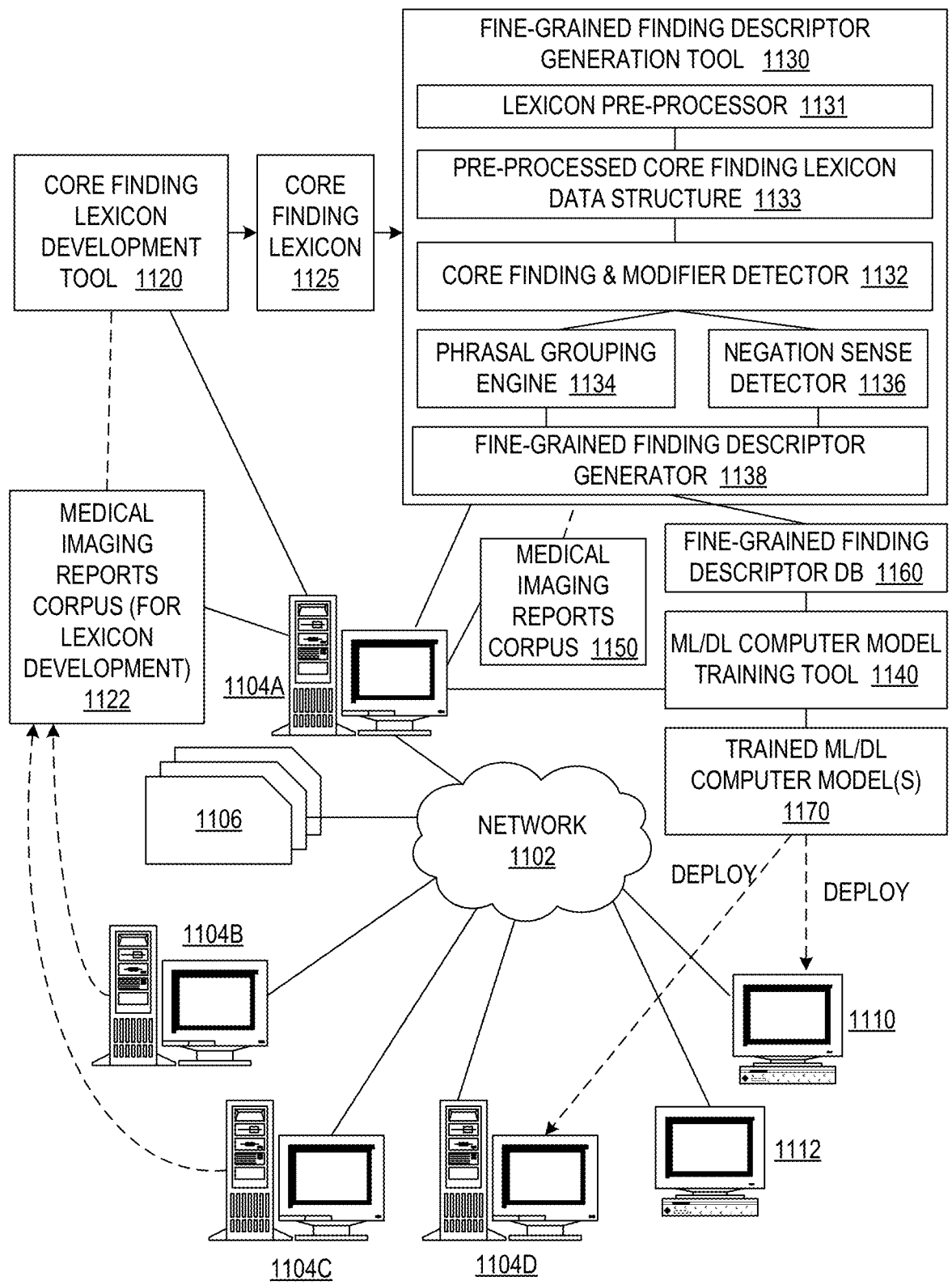
FIG. 11 depicts a pictorial representation of an example distributed data processing system in which aspects of the illustrative embodiments may be implemented.
Figure 12:
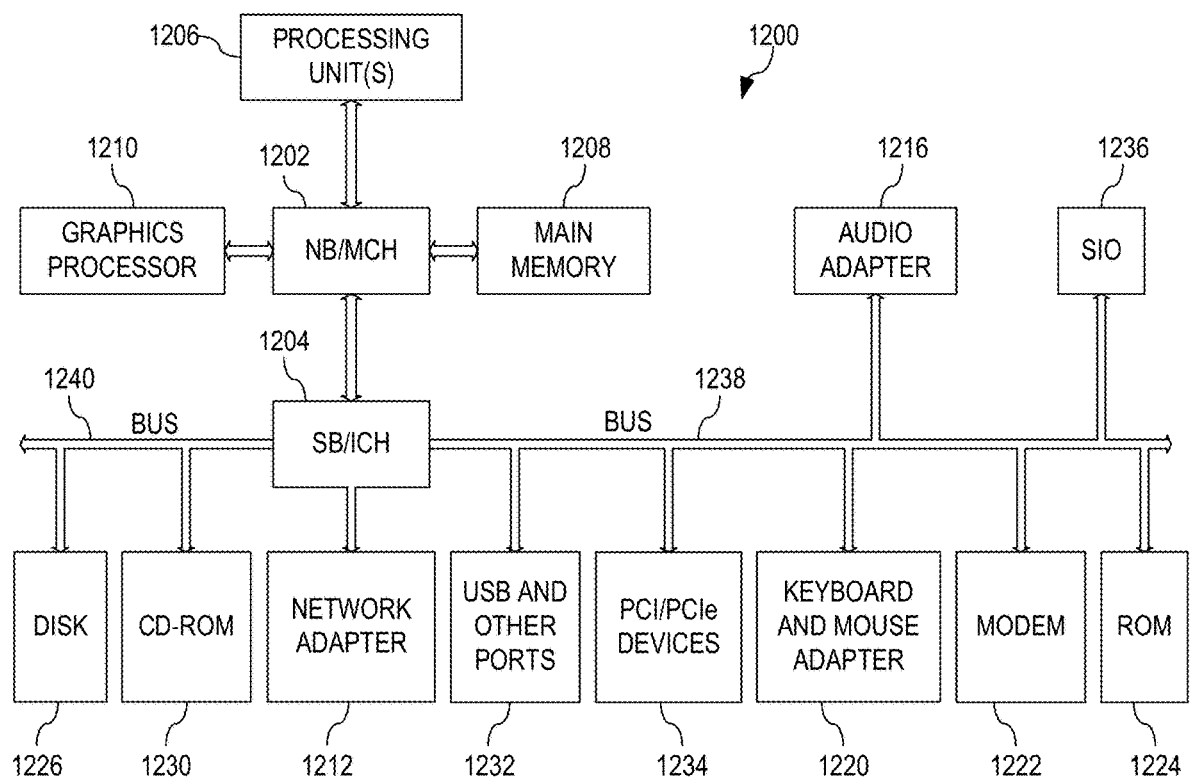
FIG. 12 is a block diagram of one example data processing system in which aspects of the illustrative embodiments may be implemented.

As the present invention is specifically directed to improved automated computing tools and automated computing tool methodologies, it can be appreciated that the illustrative embodiments may be utilized in many different types of data processing environments in which one or more computing devices are specifically configured through software/hardware logic to perform the specific automated computing tool processes previously described above. In order to provide a context for the description of the specific elements and functionality of the illustrative embodiments, FIGS. 11 and 12 are provided hereafter as example environments in which aspects of the illustrative embodiments may be implemented. It should be appreciated that FIGS. 11 and 12 are only examples and are not intended to assert or imply any limitation with regard to the environments in which aspects or embodiments of the present invention may be implemented. Many modifications to the depicted environments may be made without departing from the spirit and scope of the present invention.

FIG. 11 depicts a pictorial representation of an example distributed data processing system in which aspects of the illustrative embodiments may be implemented. Distributed data processing system 1100 may include a network of computers in which aspects of the illustrative embodiments may be implemented. The distributed data processing system 1100 contains at least one network 1102, which is the medium used to provide communication links between various devices and computers connected together within distributed data processing system 1100. The network 1102 may include connections, such as wire, wireless communication links, or fiber optic cables.

In the depicted example, servers 1104A-D are connected to network 1102 along with network attached storage unit 1108. In addition, client computing devices 1110, 1112, and 1114 are also connected to network 1102. These client computing devices 1110, 1112, and 1114 may be, for example, personal computers, network computers, proprietary servers, or the like. In the depicted example, one or more of the servers 1104A-D provides data, such as boot files, operating system images, and/or applications to the client computing devices (clients) 1110, 1112, and 1114. Client computing devices 1110, 1112, and 1114 are clients to servers 1104A-D in the depicted example. Distributed data processing system 1100 may include additional servers, clients, and other devices not shown.

In the depicted example, distributed data processing system 1100 is the Internet with network 1102 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, the distributed data processing system 100 may also be implemented to include a number of different types of networks, such as for example, an intranet, a local area network (LAN), a wide area network (WAN), or the like. As stated above, FIG. 11 is intended as an example, not as an architectural limitation for different embodiments of the present invention, and therefore, the particular elements shown in FIG. 11 should not be considered limiting with regard to the environments in which the illustrative embodiments of the present invention may be implemented.

As shown in FIG. 11, one or more of the computing devices, e.g., server 1104A, may be specifically configured to implement a core finding lexicon development computing tool 1120, a fine-grained finding descriptor generation computing tool 1130, a machine learning/deep learning (ML/DL) computer model training computing tool 1140 in accordance with one or more of the illustrative embodiments described herein. The configuring of the computing device(s) may comprise the providing of application specific hardware, firmware, or the like to facilitate the performance of the operations and generation of the outputs described herein with regard to the illustrative embodiments. The configuring of the computing device(s) may also, or alternatively, comprise the providing of software applications stored in one or more storage devices and loaded into memory of the computing device(s), such as server 1104A, for causing one or more hardware processors of the computing device to execute the software applications that specifically configure the processors to perform the operations and generate the outputs described herein with regard to the illustrative embodiments. Moreover, any combination of application specific hardware, firmware, software applications executed on hardware, or the like, may be used without departing from the spirit and scope of the illustrative embodiments. In this way, the computing device(s) configured to perform the computer specific operations of the present invention are specialized computing devices performing computer operations based on computer specific logical structures in a manner that cannot be practically performed manually or through human mental processes.

That is, it should be appreciated that once the computing device(s) is/are configured in one of these ways, the computing device becomes a specialized computing device specifically configured to implement the mechanisms of the illustrative embodiments and is not a general purpose computing device. Moreover, as described herein, the implementation of the mechanisms of the illustrative embodiments improves the functionality of the computing device and provides a useful and concrete result that facilitates a computer specific automated learning of fine-grained finding labels used in medical imaging reports and the automated training of machine learning/deep learning computer models to perform artificial intelligence (cognitive computing) operations based on the automatically learned fine-grained finding labels.

The core finding lexicon development computing tool 1120 is specifically configured to perform the operations described previously (see the section of the description above entitled "Fine-Grained Finding Descriptor and Core Finding Vocabulary"), either automatically or semi-automatically, to perform core findings and modifier detection. The core finding lexicon development computing tool 1120 may operate automatically or semi-automatically to process a corpus 1122 of medical imaging reports and medical imaging data to identify core findings terms/phrases in these medical and a core set of modifier types, such that these core findings terms/phrases may be used to generate an initial core findings lexicon/vocabulary. In one illustrative embodiment, the core finding lexicon development computing tool identifies all of the instances of core findings in the electronic documents, e.g., medical imaging reports and corresponding medical image data, in the corpus 1122 and presents these core findings to subject matter experts (SMEs) for evaluation as to whether or not the core finding should be maintained as part of the lexicon.

As discussed above, the core finding lexicon development computing tool 1120 uses a vocabulary-driven concept extraction algorithm to spot all occurrences of core concepts and/or their variants, e.g., synonyms, misspellings, alternative forms, etc., in an electronic corpus of electronically stored medical imaging reports. For example, using a chest X-ray embodiment, the vocabulary-driven concept extraction algorithm is used to create a core finding lexicon or vocabular to catalog all possible findings in medical images, such as chest x-rays, for example, which recorded the names, spelling variants, synonyms, etc. for core findings and modifiers by analyzing a large set of electronically stored medical imaging reports, e.g., 200,000 medical imaging reports. The core finding lexicon development computing tool 1120 generates an initial core finding lexicon or vocabulary data structure 1125 that specifies the core findings and their corresponding finding types and initial set of modifier types, and corresponding modifier instances (see FIG. 4). This core finding lexicon data structure 1125 may then be used by the fine-grained finding descriptor generation computing tool 1130 to identify instances of core findings in medical imaging report data structures of a corpus of such medical imaging report data structures, and generate fine-grained finding descriptor data structures based on the identified instances.

The fine-grained finding descriptor generation computing tool 1130 includes a core finding and modifier detector 1132, a phrasal grouping engine 1134, a negation sense detector 1136, and a fine-grained finding descriptor generator 1138. The core finding and modifier detector 1132 uses the core finding lexicon data structure 1125 and a vocabulary-driven concept extraction algorithm to identify occurrences of core concepts and their variants in natural language content of a corpus of medical imaging reports 1150, which may be the same, different, or overlapping corpus of medical imaging reports as the one used for lexicon development 1122. The fine-grained finding descriptor generation computing tool 1130, in some illustrative embodiments, uses a lexicon pre-processor 1131 implementing a smallest prefix building algorithm to pre-process the core finding lexicon (vocabulary) data structure 1125 to ensure high precision. The lexicon pre-processor 1131 uses a dynamic programming algorithm to align the words of candidate vocabulary phrases to portions of natural language content in the medical imaging reports 1150 using the smallest prefixes with the resulting alignment guaranteeing the largest number of words of the vocabulary phrase being matched to the largest possible extent in the portion of natural language content while still maintaining the word order and allowing missed and spurious words in-between, as described previously. In order to ensure high recall, the vocabulary-driven concept extraction algorithm of the core finding and modifier detector 1132 uses a longest common subfix (LCF) algorithm to perform an approximate match to a target vocabulary phrase in the pre-processed core finding lexicon data structure 1133 within a portion of natural language content of a medical imaging report 1150. In this way, phrases in the natural language that are believed to contain core findings and/or modifiers may be identified.

The phrasal grouping engine 1134 uses a natural language processing (NLP) parser, such as an English Slot Grammar (ESG) parser in some illustrative embodiments, to parse the natural language content of a medical imaging report 1150 to generate a dependency parse tree. The phrasal grouping engine 1134 operates on the dependency parse tree to perform connected component clustering based on the placement of terms in the parse tree, e.g., based on a slot grammar placement of the terms. Core findings and modifiers are then identified within each grouping and associated with each other or with adjacent groups, as previously described above. In this way, the phrasal grouping engine 1134 identifies instances of core findings and corresponding modifiers in medical imaging reports which can be used to create the fine-grained finding descriptor data structures.

The negation sense detector 1136 performs the operations described previously for detecting negation of core findings in the natural language content of the medical imaging report. For example, in some illustrative embodiments, a two-step process is utilized that combines language structuring and vocabulary-based negation detection. The language structuring based negation detection starts from the dependency parse tree of the natural language content and looks for known dependency patterns corresponding to negation, as specified in a predefined set of known dependency patterns and using pattern matching to find matching patterns in the given dependency parse tree. In this way, negation keywords are identified in the dependency parse tree and the scope of words encompassed by these negation keywords is identified by the known negation dependency patterns. The negation pattern detection algorithm iteratively identifies words within the scope of negation based on dependency parsing. To ensure that the negation modifiers are being associated with the relevant core phrase, a vocabulary of "negation prior" and "negation post" terms is also used such that detection of their occurrence prior or post the core finding is used as a further indication of negation or avoiding spurious negation detection. Negation detected by the negation sense detector 1136 is used to set a corresponding negation attribute in the fine-grained finding descriptor data structure.

The fine-grained finding descriptor generator 1138 generates the fine-grained finding descriptors corresponding to the instances of core findings and associated modifiers found in the various medical imaging reports of the corpus of medical imaging reports 1150. As discussed previously, the illustrative embodiments utilize a new fine-grained finding descriptor data structure to define fine-grained finding patterns found in natural language content of medical imaging reports. In some illustrative embodiments, this fine-grained finding descriptor takes the form of $F_i = <T_i|N_i|C_i|M_i^*>$ where again $F_i$ is the fine-grained label, $T_i$ is the finding type, $N_i$=yes|no and indicates a positive or ruled-out finding, $C_i$ is the core finding itself, and $M_i$ are one or more of the possible finding modifiers. While this format is used in some of the illustrative embodiment, the illustrative embodiments are not limited to this format. Other forms and formats of descriptor data structures that associate core findings with modifiers of the core findings may be used without departing from the spirit and scope of the present invention.

With the above format of a fine-grained finding descriptor as an example implementation, the attributes, or fields, of the descriptor are populated with the resulting fine-grained finding information obtained through the operation of the other elements 1132-1136 of the fine-grained finding descriptor generation computing tool 1130. That is, the core finding attribute $C_i$ is populated with the core finding from the lexicon 1125 for which a match was found in a medical imaging report of the corpus 1150 by the core finding and modifier detector 1132. Similarly, the core finding type $T_i$ is populated with information present in the lexicon 1125 specified through the lexicon 1125 building process implemented by the core finding lexicon development computing tool 1120, e.g., see first column in FIG. 2 and the category column in FIG. 4. The modifiers $M_i$ are populated by the modifiers discovered through the phrasal grouping operations performed by the phrasal grouping engine 1134. The negation attribute Ni is populated with a value corresponding to whether or not the core finding was determined, by the negation sense detector 1136, to be negatively indicated by other natural language content in the medical imaging report 1150.

Thus, the fine-grained finding descriptor generator 1138 generates a fine-grained finding descriptor data structure, e.g., $F_i = <T_i|N_i|C_i|M_i^*>$, for each instance of a core finding found in each medical imaging report processed from the corpus 1150. The generated fine-grained finding descriptor data structures may be stored temporally for further evaluation as to whether or not they should be maintained in a fine-grained finding descriptor database 1160 for training ML/DL computer models. The evaluation of whether or not to maintain certain fine-grained finding descriptor data structures may be determined based on various automatically applied criteria applied by the fine-grained finding descriptor generator 1138, and may include SME review in some illustrative embodiments. The automatically applied criteria, for example, may be a frequency of occurrence within the corpus 1150 compared to a predetermined threshold, e.g., 100. That is, the number of instances of the negatively/positively indicated core finding and modifiers specified in the fine-grained finding descriptor data structure being present within the corpus 1150 is calculated from the generated descriptors and the number of instances are compared to the predetermined threshold value. If the number of instances equals or exceeds the threshold, then an instance of the fine-grained finding descriptor data structure is maintained in the database 1160.

Alternatively, the fine-grained finding descriptor generator 1138 may not generate and store a separate instance of the fine-grained finding descriptor data structure for every instances of the same negatively/positively indicated core finding and modifiers. To the contrary, the fine-grained finding descriptor generator 1138 may generate the fine-grained finding descriptor data structure and compare it to previously generated fine-grained finding descriptor data structure to determine if there is already a matching fine-grained finding descriptor that was generated. If there is a matching fine-grained finding descriptor, then a counter associated with the matching fine-grained finding descriptor data structure is incremented. Thus, a single fine-grained finding descriptor data structure is generated for instances of each different fine-grained finding descriptor found in the corpus 1150 with a counter being used to maintain a count of how many instances of that fine-grained finding descriptor were found to be present in the corpus 1150. This counter value may then be used to compare to the predetermined threshold to determine whether to maintain the fine-grained finding descriptor data structure as part of the database 1160 or not.

As a result of the above processes of the fine-grained finding descriptor generation computing tool 1130, a database 1160 of fine-grained finding descriptor data structures is generated. The fine-grained finding descriptors, or fine-grained finding labels (FFLs), represented in these data structures of the database 1160 may be used to train ML/DL computer models for performing various types of artificial intelligence (cognitive computing) computer operations on new input data. That is, the database 1160 may be accessed by the ML/DL computer model training computing tool 1140 in accordance with one or more of the illustrative embodiments described herein, to train a ML/DL computer model for a specific purpose, such that the trained ML/DL computer model 1170 applies its machine learned specialized training to evaluate new data and provide useful results that are not able to be obtained through generic computing operations, such as loads, stores, basic computer mathematical operations, and the like. It should be appreciated that the resulting trained ML/DL computer model 1170 need not be executed on the same computing device or devices on which the ML/DL computer model training computing tool 1140 executes, and in fact the ML/DL computer model training computing tool 1140 may also execute on a different computing device from the core finding lexicon development computing tool 1120 and/or the fine-grained finding descriptor generation computing tool 1130. That is, each of the elements 1120-1170 may in fact be implemented on different computing devices in the computing environment.

In some illustrative embodiments, the ML/DL computer model training computing tool 1140 may train different instances of the ML/DL computer model 1170 which are each separately deployed for runtime execution on the same or different computing devices and/or may train a single ML/DL computer model which is then deployed to the same or different computing devices as separate instances. Furthermore, in some embodiments, the ML/DL computer model training computing tool 1140 may perform training of a ML/DL computer model remotely such that the ML/DL computer model stays on a user's local computing device, but is trained through a machine learning process in which the ML/DL computer model training computing tool 1140 provides the inputs to the ML/DL computer model, receives the outputs from the ML/DL computer model, and adjusts operational parameters of the ML/DL computer model to reduce loss/error in the outputs of the ML/DL computer model.

As mentioned above, the ML/DL computer model may be trained to perform various types of artificial intelligence (cognitive computing) operations. An example of one type of artificial intelligence operation, for which a ML/DL computer model may be trained based on the fine-grained finding descriptors or fine-grained finding labels (FFLs) in the database 1160, is medical image labeling. That is, the ML/DL computer model 1170 may be trained to take, as input, a medical image data structure, perform image analysis on the medical image data structure, such as a pattern recognition operation on the medical image, and label structures, anomalies, and the like, in the medical image with fine-grained finding labels by matching the patterns found in the medical image with corresponding fine-grained finding descriptor data structures in the database 1160. The information in the fine-grained finding descriptor data structures may be used to generate the actual labels that are applied to the patterns in the medical image to thereby generate fine-grained finding labeled medical image data which provides greater insights into the internal medical condition of patients. The resulting fine-grained finding labeled medical image data may be used as a basis for presentation of the medical images along with the fine-grained finding labels pinpointing the structures/anomalies in the medical image and the fine-grained findings corresponding to those structures/anomalies. Again, an example ML/DL computer model for medical image labeling using the database 1160 is shown in FIG. 10 and described above.

With regard to training the ML/DL computer model 1170, as discussed previously, each FFL pattern can be denoted by an label identifier which can be used to perform machine learning training of the ML/DL computer model 1170, where the ML/DL computer model 1170 is given a training image and its corresponding label vector indicating all the FFL patterns present (1 if the image contains a particular FFL pattern and 0 otherwise). The task of the machine learning is to learn a function that maps the extracted image features/patterns to those labels in the label vector such that when similar image features/patterns are detected in non-labeled images, the trained ML/DL computer model 1170 is able to map those features/patterns to predicted FFL patterns and generate probability values or scores indicating the likelihood that the FFL pattern applies to the input non-labeled image.

The trained ML/DL computer model 1170 may also be trained for various other operations, such as patient medical condition synopsis or summary generation, for example. That is, the ML/DL computer model 1170 may be trained using the database 1160 to identify instances of the FFLs defined by the descriptor data structures present in the database 1160 in patient electronic medical records, which may include medical imaging reports as well as other electronically stored medical information from various source computing systems, e.g., pharmacies, doctor offices, hospitals, medical laboratories, medical imaging companies, medical supply stores, etc. This patient medical information data may be compiled from the various source computing systems into one or more electronic medical records that may be processed by the trained ML/DL computer model 1170 or a plurality of trained ML/DL computer models, of which the trained ML/DL computer model 1170 may be one, in order to generate a summary of the relevant patient medical condition information to be presented to a medical practitioner, such as based on a current medical condition of the patient, based on a specific query submitted by the medical practitioner, or the like.

For example, the trained ML/DL computer model 1170 may be trained to classify text in the patient electronic medical record by extracting features from the text and matching them with the core findings and modifiers specified in the FFLs defined by the fine-grained finding descriptor data structures of the database 1160. In this case, there may be a separate class associated with each FFL of each fine-grained finding descriptor data structure and the ML/DL computer model 1170 is trained, through a machine learning process, to evaluate features extracted from the text of the patient electronic medical records and predict whether the pattern of features matches one or more of the FFLs. The fine-grained finding descriptor data structure(s) associated with the classification prediction(s) made by the trained ML/DL computer model 1170 may be used as a basis for composing a natural language description of the findings as an indicator of a medical condition of the patient. For example, the matching portions of text from the patient electronic medical record may be identified and provided as part of the patient summary and the core finding, modifiers, and negation attributes of the fine-grained finding descriptor data structure may be used as a basis for composing a natural language representation of the FFL of the fine-grained finding descriptor data structure. This is just one example of one way in which a patient summary generation AI operation may be implemented by a trained ML/DL computer model 1170 trained using the database 1160 generated by the processes of the illustrative embodiments.

As noted above, the mechanisms of the illustrative embodiments utilize specifically configured computing devices, or data processing systems, to perform the operations for developing a core finding lexicon, generating fine-grained finding descriptors based on the core finding lexicon, and training a ML/DL computer model based on the FFLs defined in the fine-grained finding descriptors. These computing devices, or data processing systems, may comprise various hardware elements which are specifically configured, either through hardware configuration, software configuration, or a combination of hardware and software configuration, to implement one or more of the systems/subsystems described herein. FIG. 12 is a block diagram of just one example data processing system in which aspects of the illustrative embodiments may be implemented. It should be appreciated that while FIG. 12 may resemble other diagrams of data processing systems, the data processing systems and computing devices implementing the illustrative embodiments are not generic computing devices. They are specialized computing devices that are specifically configured to perform the non-generic computer operations realizing the functions and operations described herein in an automated or semi-automated manner. These operations described herein are specific improved computer operations that can only be performed by a specialized data processing system, computing device, or computer tool that is specifically configured to perform these operations which cannot be practically performed within a human mind.

Data processing system 1200 is an example of a computer, such as server 1104 in FIG. 11, in which computer usable code or instructions implementing the processes and aspects of the illustrative embodiments of the present invention may be located and/or executed so as to achieve the operation, output, and external effects of the illustrative embodiments as described herein. In the depicted example, data processing system 1200 employs a hub architecture including north bridge and memory controller hub (NB/MCH) 1202 and south bridge and input/output (I/O) controller hub (SB/ICH) 1204. Processing unit 1206, main memory 1208, and graphics processor 1210 are connected to NB/MCH 202. Graphics processor 1210 may be connected to NB/MCH 1202 through an accelerated graphics port (AGP).

In the depicted example, local area network (LAN) adapter 1212 connects to SB/ICH 1204. Audio adapter 1216, keyboard and mouse adapter 1220, modem 1222, read only memory (ROM) 1224, hard disk drive (HDD) 1226, CD-ROM drive 1230, universal serial bus (USB) ports and other communication ports 1232, and PCI/PCIe devices 1234 connect to SB/ICH 1204 through bus 1238 and bus 1240. PCI/PCIe devices may include, for example, Ethernet adapters, add-in cards, and PC cards for notebook computers. PCI uses a card bus controller, while PCIe does not. ROM 1224 may be, for example, a flash basic input/output system (BIOS).

HDD 1226 and CD-ROM drive 1230 connect to SB/ICH 204 through bus 1240. HDD 1226 and CD-ROM drive 1230 may use, for example, an integrated drive electronics (IDE) or serial advanced technology attachment (SATA) interface. Super I/O (SIO) device 1236 may be connected to SB/ICH 1204.

An operating system runs on processing unit 1206. The operating system coordinates and provides control of various components within the data processing system 1200 in FIG. 12. As a client, the operating system may be a commercially available operating system such as Microsoft® Windows 10®. An object-oriented programming system, such as the Java™ programming system, may run in conjunction with the operating system and provides calls to the operating system from Java™ programs or applications executing on data processing system 1200.

As a server, data processing system 1200 may be, for example, an IBM eServer™ System p® computer system, Power™ processor based computer system, or the like, running the Advanced Interactive Executive (AIX®) operating system or the LINUX® operating system. Data processing system 1200 may be a symmetric multiprocessor (SMP) system including a plurality of processors in processing unit 1206. Alternatively, a single processor system may be employed.

Instructions for the operating system, the object-oriented programming system, and applications or programs are located on storage devices, such as HDD 1226, and may be loaded into main memory 1208 for execution by processing unit 1206. The processes for illustrative embodiments of the present invention may be performed by processing unit 1206 using computer usable program code, which may be located in a memory such as, for example, main memory 1208, ROM 1224, or in one or more peripheral devices 1226 and 1230, for example.

A bus system, such as bus 1238 or bus 1240 as shown in FIG. 12, may be comprised of one or more buses. Of course, the bus system may be implemented using any type of communication fabric or architecture that provides for a transfer of data between different components or devices attached to the fabric or architecture. A communication unit, such as modem 1222 or network adapter 1212 of FIG. 12, may include one or more devices used to transmit and receive data. A memory may be, for example, main memory 1208, ROM 1224, or a cache such as found in NB/MCH 1202 in FIG. 12.

As mentioned above, in some illustrative embodiments the mechanisms of the illustrative embodiments may be implemented as application specific hardware, firmware, or the like, application software stored in a storage device, such as HDD 1226 and loaded into memory, such as main memory 1208, for executed by one or more hardware processors, such as processing unit 1206, or the like. As such, the computing device shown in FIG. 12 becomes specifically configured to implement the mechanisms of one or more of the illustrative embodiments and specifically configured to perform the operations and generate the outputs described herein with regard one or more of the core finding lexicon development, fine-grained finding descriptor generation, ML/DL computer model training, and automated medical imaging report generation, in accordance with one or more of the illustrative embodiments.

Those of ordinary skill in the art will appreciate that the hardware in FIGS. 11 and 12 may vary depending on the implementation. Other internal hardware or peripheral devices, such as flash memory, equivalent non-volatile memory, or optical disk drives and the like, may be used in addition to or in place of the hardware depicted in FIGS. 11 and 12. Also, the processes of the illustrative embodiments may be applied to a multiprocessor data processing system, other than the SMP system mentioned previously, without departing from the spirit and scope of the present invention.

Moreover, the data processing system 1200 may take the form of any of a number of different data processing systems including client computing devices, server computing devices, a tablet computer, laptop computer, telephone or other communication device, a personal digital assistant (PDA), or the like. In some illustrative examples, data processing system 1200 may be a portable computing device that is configured with flash memory to provide non-volatile memory for storing operating system files and/or user-generated data, for example. Essentially, data processing system 1200 may be any known or later developed data processing system without architectural limitation.

Figure 13:
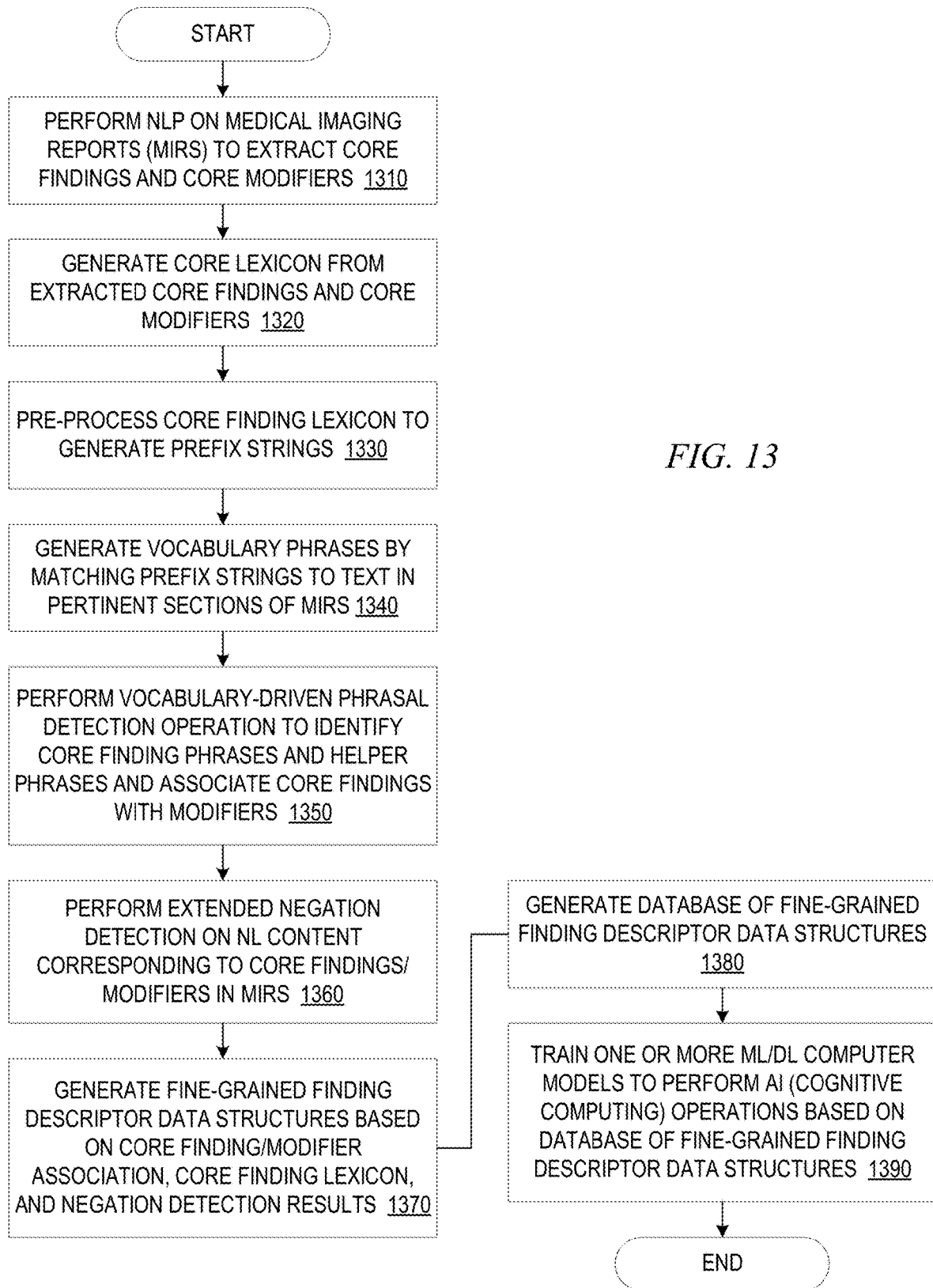
FIG. 13 is a flowchart outlining an example operation for generating fine-grained finding descriptor data structures from medical imaging reports and using those fine-grained finding descriptor data structures to train a machine learning computer model in accordance with one illustrative embodiment.

FIG. 13 is a flowchart outlining an example operation for generating fine-grained finding descriptor data structures from medical imaging reports and using those fine-grained finding descriptor data structures to train a machine learning computer model in accordance with one illustrative embodiment. The operation outlined in FIG. 13 may be performed, for example, by one or more specifically configured computing devices of one or more data processing systems, which are specifically configured to implement the core finding lexicon development computing tool 1120, the fine-grained finding descriptor generation computing tool 1130, and the machine learning/deep learning (ML/DL) computer model training computing tool 1140 in FIG. 11 and their corresponding computing operations to develop a core finding lexicon, use the developed core finding lexicon to generate fine-grained finding descriptors that define fine-grained finding labels (FFLs), and train a ML/DL computer model to perform an AI operation based on the FFLs and their fine-grained finding descriptor data structures.

As shown in FIG. 13, the operation starts by performing natural language processing and computer textual analysis on a first corpus of medical imaging report data structures to extract core findings and core modifiers used in natural language content or text of medical imaging reports (step 1310). The extracted core findings and core modifiers are evaluated through an automated and/or semi-automated process to identify a subset of core findings and core modifiers to be retrained as part of a core finding lexicon or vocabulary (step 1320). The core finding lexicon/vocabulary may include the core finding and core modifiers/modifier types, as well as other information associated with the core findings, such as finding type or the like.

The core finding lexicon/vocabulary is pre-processed using a smallest prefix building algorithm (step 1330) and the prefix strings are used as a basis to search, using a dynamic programming algorithm, such as a longest common subfix (LCF) based algorithm, for instances of the prefix strings in text of relevant sections of medical imaging reports, e.g., the indications and findings sections of medical imaging reports, to generate vocabulary phrases (step 1340). The vocabulary phrases are used as a basis for performing a vocabulary-driven phrasal detection operation that identifies core finding phrases and helper phrases and associates core findings with modifiers based on these detected phrases (step 1350). The modifiers in the illustrative embodiments described herein may be any clinical attribute that is descriptive of the core finding and thus, indicates a fine-grained specific type of the core finding. For example, the modifiers may specify clinical attributes such as laterality, anatomical location, severity, appearance characteristics, and the like.

Extended negation detection, extended by the use of pre- and post-negation term identification operations, is performed on the natural language content or text corresponding the instances of core findings and modifiers found in medical imaging reports through the above operations (step 1360). Based on the results of the association of core findings with modifiers, the core finding lexicon, and the extended negation detection, fine-grained finding descriptor data structures are generated for defining fine-grain descriptors or labels (FFLs) (step 1370). All non-duplicative descriptors, or a subset of the generated fine-grained finding descriptor data structures as determined in accordance with predefined selection criteria, may be maintained in a database for training machine learning/deep learning (ML/DL) computer models (step 1380). Thereafter, the database is used, along with machine learning training logic, to train one or more ML/DL computer models which are then deployed to perform artificial intelligence (cognitive computing) operations, such as medical image analysis, medical image augmentation (or labeling), automated patient summary generation based on patient electronic medical records, or automated medical imaging report generation (described hereafter) (step 1390). The operation then terminates.

Thus, the illustrative embodiments provide mechanisms for computer executed automatic learning of fine-grained finding labels (FFLs) from medical imaging report data structures and automatic generation of descriptor data structures that can be used to train machine learning/deep learning models to identify instances of such FFLs or patterns representative of such FFLs in other textual and/or image input data. This automated improved computing tool provides an improved computing tool methodology that permits a relatively small set of coarse-grained core findings to be used to automatically learn a larger set of fine-grained findings. The fine-grained findings then permit machine learning/deep learning models to be trained to identify much more specific structures/anomalies and provide more detailed information about such specific structures/anomalies. As a result, more focused and accurate information is able to be provided to medical practitioners, which in turn reduces sources of error in treatment of patients.

Automated Medical Imaging Report Generation

The training of machine learning/deep learning models based on FFLs may be used to perform various artificial intelligence and cognitive computing tasks as noted previously. As an additional feature of some illustrative embodiments, the training of machine learning/deep learning models may be employed as part of an artificial intelligence/cognitive computing system that operates to automatically generate medical imaging reports based on an input medical image. It should be appreciated that for this illustrative embodiment, the FFLs need not be generated using the previously described mechanisms and may be provided through other means. For example, the FFLs may be manually populated in some illustrative embodiments rather than having an automated mechanism as previously described which generates the FFLs based on the core finding lexicon. Thus, while illustrative embodiments for automated medical imaging report generation will be described where the FFLs are generated using the automated mechanisms previously described, the present invention is not limited to such and there are other embodiments contemplated which include the inventive features described hereafter, but with other sources of FFLs utilized. The automated medical imaging report generation does not require the automated mechanisms for generation of an FFL pattern database as previously described above.

Automated medical imaging report generation can greatly assist medical practitioners by providing improved computing tools that can quickly and accurately identify findings in medical images that should be brought to the attention of the medical practitioner and/or patient so that appropriate treatments may be evaluated to improve the medical condition of the patient. With advancements in artificial intelligence (AI), such as the machine learning/deep learning computer models and mechanisms such as those described herein, computing tools may be developed to perform automated preliminary reads of medical imaging data which can expedite clinical workflows, improve accuracy, and reduce overall costs. However, known mechanism for image captioning in computer vision are limited to a predefined set of semantic topics or limited coarse grained findings. Such mechanisms are not clinically acceptable as they do not ensure the correct detection of a comprehensive set of findings nor the descript of their clinical attributes, such as laterality, anatomical location, severity, etc. To the contrary, the focus of known mechanisms is on the report language generation rather than the visual detection of findings.

In further illustrative embodiments of the present invention, mechanisms are provided for performing automated medical imaging report generation based on fine-grained finding labels learned through an automated learning process, such as that described previously. As mentioned above, in one illustrative embodiment, the mechanisms described above for generating the database of FFL descriptor data structures may be used to train ML/DL computer models, such as neural networks or the like, for performing fine-grained label detection in medical image data input which determines, for a given input medical image, which fine-grained labels (FFLs) are indicated by image features extracted from the input medical image. That is, feature extraction is performed on the medical image in a manner generally known in the art, and these features are then input to a trained ML/DL computer model that associates the pattern of features with a classification corresponding to a FFL descriptor data structure generated through a process corresponding to one or more of the illustrative embodiments described above. Again, an example of a ML/DL computer model trained for performing such operations is described in FIG. 10 above. As discussed previously, in some illustrative embodiments, two models are trained in this manner, one based on core finding labels and another on the FFL labels that have support in a predetermined number of medical images, e.g., 100, such that the training exploits the mutually reinforcing nature of the coarse-fine labels.

With regard to automated medical imaging report generation, a medical imaging report can be described, in terms of the FFL detection mechanism previously described, as a binary pattern vector $P=\{I_P(F_j)\}$ where $I_P(F_j)=1$ if the FFL label $F_j \in F$ is present in the report and $I_P(F_j)=0$ otherwise, this is also referred to herein as a FFL pattern vector P. Here F is the set of FFL labels used in training the ML/DL computer model(s) and the binary pattern vector P may have a vector slot for each FFL, whose value is set to either 1 or 0 depending on whether or not the FFL is predicted to be applicable to the extracted image features from the medical image.

During the medical imaging report database creation process, medical imaging report data structures characterized by the same binary FFL pattern vector P are collected and are ranked based on the support provided by their constituent portions of natural language content, e.g., sentences. Let $R_p=r_s$ be the collection of reports spanned by a FFL pattern vector P (i.e. the collection of reports having the same FFL pattern vector P), where again the FFL pattern vector $P=\{I_P(F_j)\}$, then $$Rank(r_s) = \sum_{j=1}^{M_s} h(s_j)$$

where $M_s$ is the number of relevant constituent portions of natural language content (e.g., sentences) in report $r_s$ spanned by one or more of the FFLs in the pattern P. Here $h(s_j)$ is given by $$h(s_j) = \frac{\text{Number of reports } r_i \text{ that contain } s_j}{|R_P|},$$

where sj is the portion of natural language content, e.g., sentence, that contains one or more of the FFL patterns. The highest ranked medical imaging reports are then stored as associated reports with the binary pattern vectors in a database, e.g., the top ranked medical imaging report, or top N ranked medical imaging reports for each FFL pattern vector, are stored in association with the FFL pattern vector.

Figure 14A:
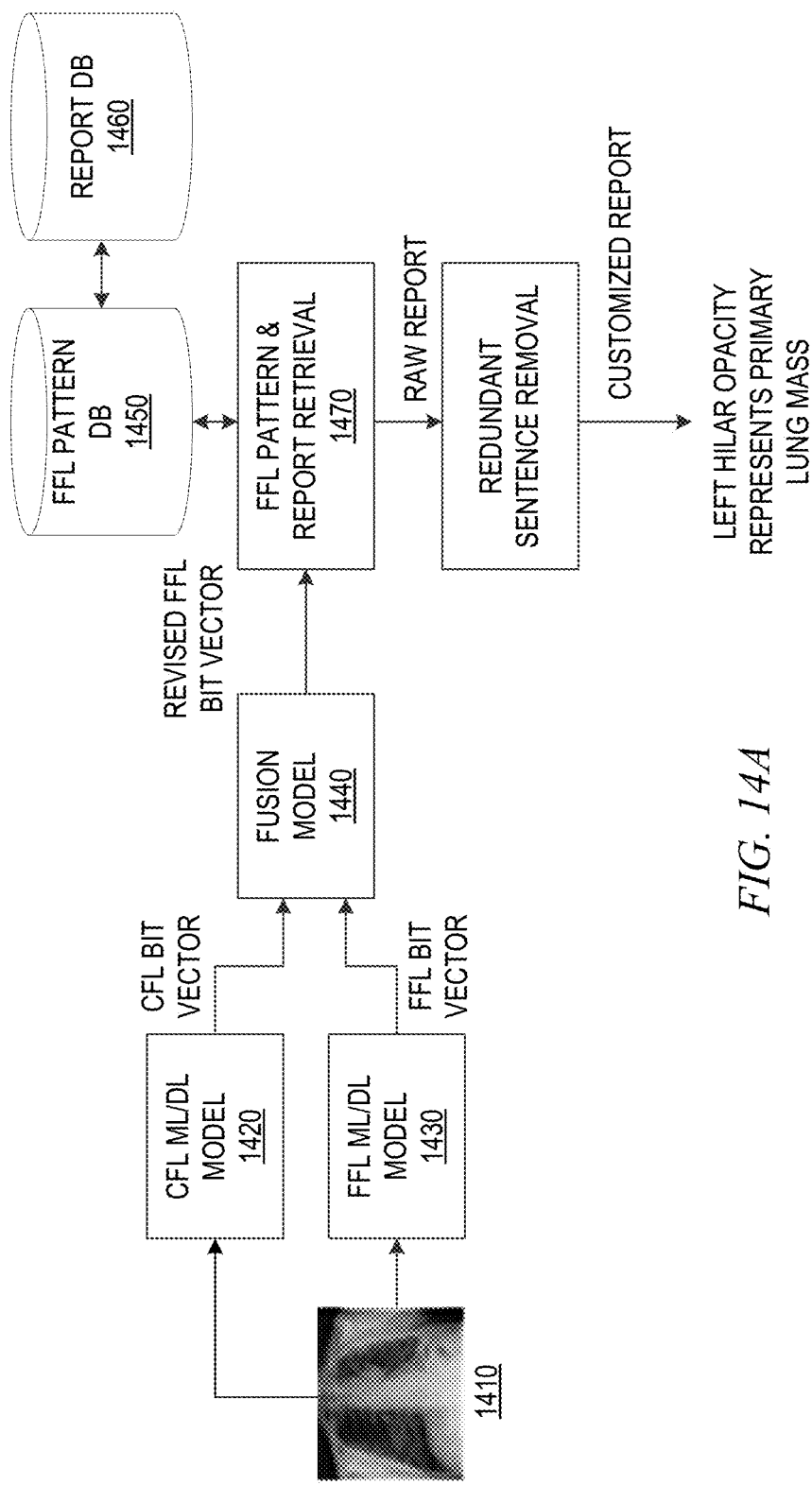
FIG. 14A is an example diagram illustrating an overall automated medical imaging report generation workflow in accordance with one illustrative embodiment.

An overall automated medical imaging report generation workflow is illustrated in FIG. 14A. As shown in FIG. 14A, a medical image data structure 1410 is fed to the two ML/DL computer models, e.g., trained neural networks, 1420 and 1430. A first one of the ML/DL computer models 1420 is trained for classifying image features extracted from the medical image data structure 1410 with regard to core finding labels (CFLs), whereas a second one of the ML/DL computer models 1430 is trained to classify features extracted from the medical image data structure 1410 with regard to FFLs, such as the FFLs defined by the fine-grained finding descriptor data structures of a database generated in a manner according to one or more of the illustrative embodiments previously described above.

The classification predictions generated by the ML/DL computer models 1430 are input to the fusion computer model 1440 where they are "thresholded" using the image based precision-recall F1-score for optimization. Thresholding is used to convert the real-number prediction scores of the ML/DL computer models 1430 to the binary scores of positives and negatives. Let $\theta$ be a vector that contains all label thresholds. To compute the optimal thresholds, an objective function based on the image-based F1 score is used:

$$L(\theta) = -\ln\left(\frac{1}{n}\sum_{i=1}^{n} F1_i(\theta)\right)$$

with $F1_i$ being the F1 score of image i and n being the number of images. The F1 score is the harmonic mean of the positive predictive value (PPV) and sensitivity, which is computed as:

$$F1 = \frac{2TP + \epsilon}{2TP + FP + FN + \epsilon}$$

Where TP, FP, and FN are the true positives, false positives, and false negatives, respectively, computed between the ground truth and the binary scores after thresholding by $\theta$. The value $\epsilon=10^{-7}$ is used to handle the 0/0 situation when there are no positives in both prediction and ground truth. The optimal $\theta$ can be computed by minimizing $L(\theta)$ through an optimization algorithm. In one illustrative embodiment, the derivative-free global optimization algorithm, ESCH, is used as it provides the best results in tested algorithms. By focusing on the positive occurrences of findings per image and minimizing $L(\theta)$ it is ensured that the prediction has as few false positives while still enabling the detection of relevant findings.

The resulting pattern vectors are combined to result in the consolidated FFL pattern vector $Q=\{I_Q(F_j)\}$ such that each CFL/FFL in the outputs of the ML/DL computer models is represented in corresponding vector slots of the consolidated FFL pattern vector Q. The best matching medical imaging reports from a medical imaging report database 1460 are then derived by the FFL pattern and report retrieval engine 1470 from the semantically nearest FFL pattern vectors in the FFL pattern database 1450. It should be noted that the FFL pattern database 1450 may be the database of fine-grained finding descriptor data structures generated through one or more of the illustrative embodiments described above.

The semantic distance between a query FFL bit pattern vector Q, generated by the fusion module 1440 and a pattern vector P from the FFL pattern database 1450 is given by:

$$d(Q, P) = \frac{\sqrt{\sum_{l=1}^{|F|} \omega_l(I_P(F_l) - I_Q(F_l))^2}}{|F|}$$

where $\omega_l$ is the weight associated with the FFL label $F_l$. A criticality rank for each core finding on a scale of 1 to 10 may be supplied by a SME, which may then be normalized and used to weight the clinical importance of a finding during matching. Once the matching FFL pattern in the database 1450 is determined, the FFL pattern and report retrieval engine 1470 determines the highest ranked medical imaging report in the report database 1460 based on a ranking of the medical imaging reports associated with the matching FFL pattern. The ranking of this subset of medical imaging reports from the report database 1460 may be performed in accordance with the ranking function $$Rank(r_s) = \sum_{j=1}^{M_s} h(s_j),$$

discussed previously, for example.

Having identified the best matching, or highest ranking, medical imaging report, the FFL pattern and report retrieval engine 1470 drops all sentences from the retrieved report whose evidence cannot be found in the FFL label pattern of the query Q, thus achieving the variety needed in returned reports per query.

Figure 14B:
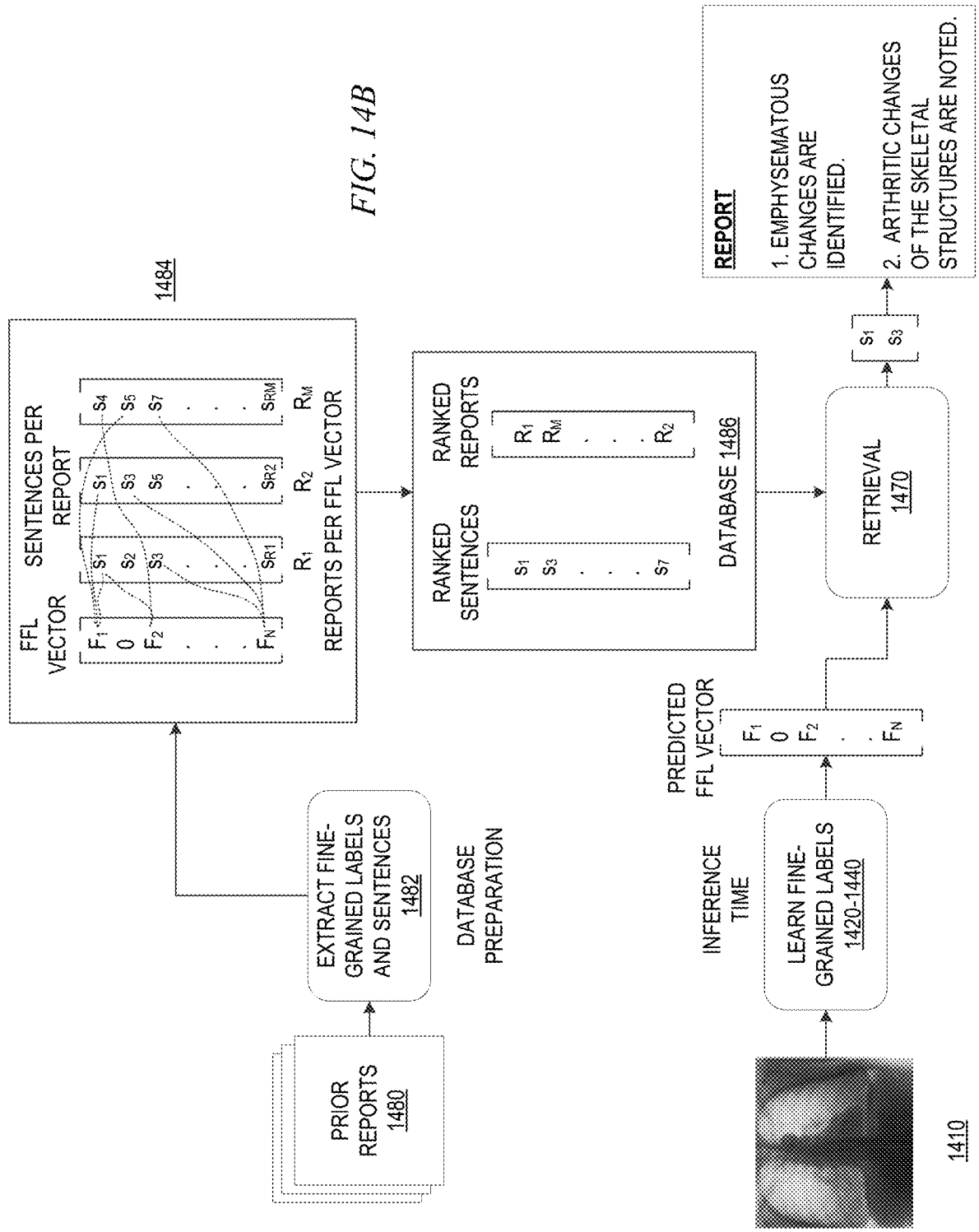
FIG. 14B is another example diagram illustrating an overall automated medical imaging report generation workflow with additional details regarding report database preparation in accordance with one illustrative embodiment.

FIG. 14B provides an example diagram of the overall automated medical imaging report generation workflow of FIG. 14A with some additional details regarding the report database 1460 preparation depicted. Referring to FIG. 14B, each of the prior report electronic documents 1480, represented as report clusters R1, R2, . . . RM which are clusters or collections of extracted portions of natural language content, e.g., sentences. Some portions/sentences can contain more than one FFL pattern such as s1 in R1 containing both F1 and F2, shown by the arrows in the reports per FFL vector 1484 generated as a result of the extraction of fine-grained labels and sentences from the prior reports 1480. Each cluster R1, R2, . . . RM in the reports per FFL vector 1484 spans a single FFL vector {F1 . . . FN}. The sentences collected across all the reports in the cluster are ranked based on their frequency of occurrence within the cluster (see 1486 in FIG. 14). Thus, s1 is ranked highest because it occurs the most across reports R1, R2, . . . RM (each occurrence per report is counted once in this analysis so that sentence repeats within a single report are avoided). The scores of each sentence are then added for all the sentences in a report R1, R2, . . . RM to obtain an overall score for the report. Note that all reports in the cluster have the same set of FFL patterns occurring (that is the definition of the cluster). Thus, the only point of selection of sentence is now down to those that are most likely to be included in prior reports 1480. In addition, since the ranked sentences are chosen from the highest ranked report R1, R2 . . . RM, after selecting the highest ranked report (R1 in this case), they are also sentences that are likely to come from a coherent report. Since not all sentences of the report R1 are selected, rather only those that cover the FFL pattern vector presence, extraneous sentences from the original report are avoided. Thus the quality of the automatically generated report 1488 is high.

The workflows shown in FIGS. 14A-14B may be implemented by one or more specifically configured computing devices of one or more data processing systems, such as those previously described above. Again, the specific configuration of these computing devices, along with the non-generic computer operations required to perform the operations described herein, renders these computing devices and data processing system specialized computing devices and data processing systems that are specifically configured to implement the mechanisms and perform the operations of the illustrative embodiments which provide an improved computing tool and improved computing tool operations. These operations are complex computer operations specifically involving artificial intelligence (cognitive computing) logic, pattern analysis, and the like, all of which are computer specific non-generic computer operations that cannot be practically performed in the human mind.

For example, in a distributed data processing environment such as the example environment shown in FIG. 11, one or more server computing devices 1104 may be configured to perform the automated medical imaging report generation workflow shown in FIG. 14. In such an implementation, the medical image data input 1410 may be obtained from any suitable source computing system, e.g., network attached data storage 1106, one or more client computing devices 1110-1112, another server computing device 1104, or the like. For example, a client computing device 1110 may be a computing device at a medical imaging equipment location which performs the examination of the patient to capture the medical image data and provides the medical image data to the specially configured server computing device 1104 via one or more data networks, for automated medical imaging report generation. The specially configured computing device 1104 may then perform the workflow of FIG. 14 to automatically generate a medical imaging report data structure which may be returned to the client computing device 1110 and/or distributed to other authorized computing devices, such as a patient's primary care physician's office computing devices. Any known or later developed manner of electronic communication may be used, for example, to exchange the data between the computing systems and/or distribute the automatically generated medical imaging report. Of course, appropriate privacy protection mechanisms, such as encryption and the like, can be used to ensure the privacy of the patient's personally identifiable information in any data exchanged, such as in the automatically generated medical imaging report.

By specifically configuring one or more computing devices of one or more data processing systems to perform automated medical imaging report generation, an improved computer tool and improved computer tool process is provided that provides significant benefits to medical practitioners. Specifically, being able to obtain automated preliminary read reports for common examinations, such as chest X-rays, MRIs, CT scans, and the like, will expedite clinical workflows, improve accuracy in such clinical workflows minimizing human error, and improve operational efficiencies of hospitals and medical practices.

The quality of the automatically generated medical imaging reports generated by the mechanisms of the illustrative embodiments is illustrated in FIG. 15 which shows examples of medical images and the corresponding medical imaging reports generated by manual processes 1510 and by the automated mechanisms 1520 of the illustrative embodiments. As can be seen from the examples in FIG. 15, the medical imaging report generated by the automated mechanism of the illustrative embodiments provides the pertinent finding information as well as modifiers and the like for finely identifying the findings in the accompanying medical images. While the automated reports generated differ in the text used to describe the medical concepts, they provide an equivalent level of detail and information about the same critical medical concepts that are identified in the manually generated reports, but instead using different automated tools and automated operations that do not require intervention of a human subject matter expert.

Figure 16:
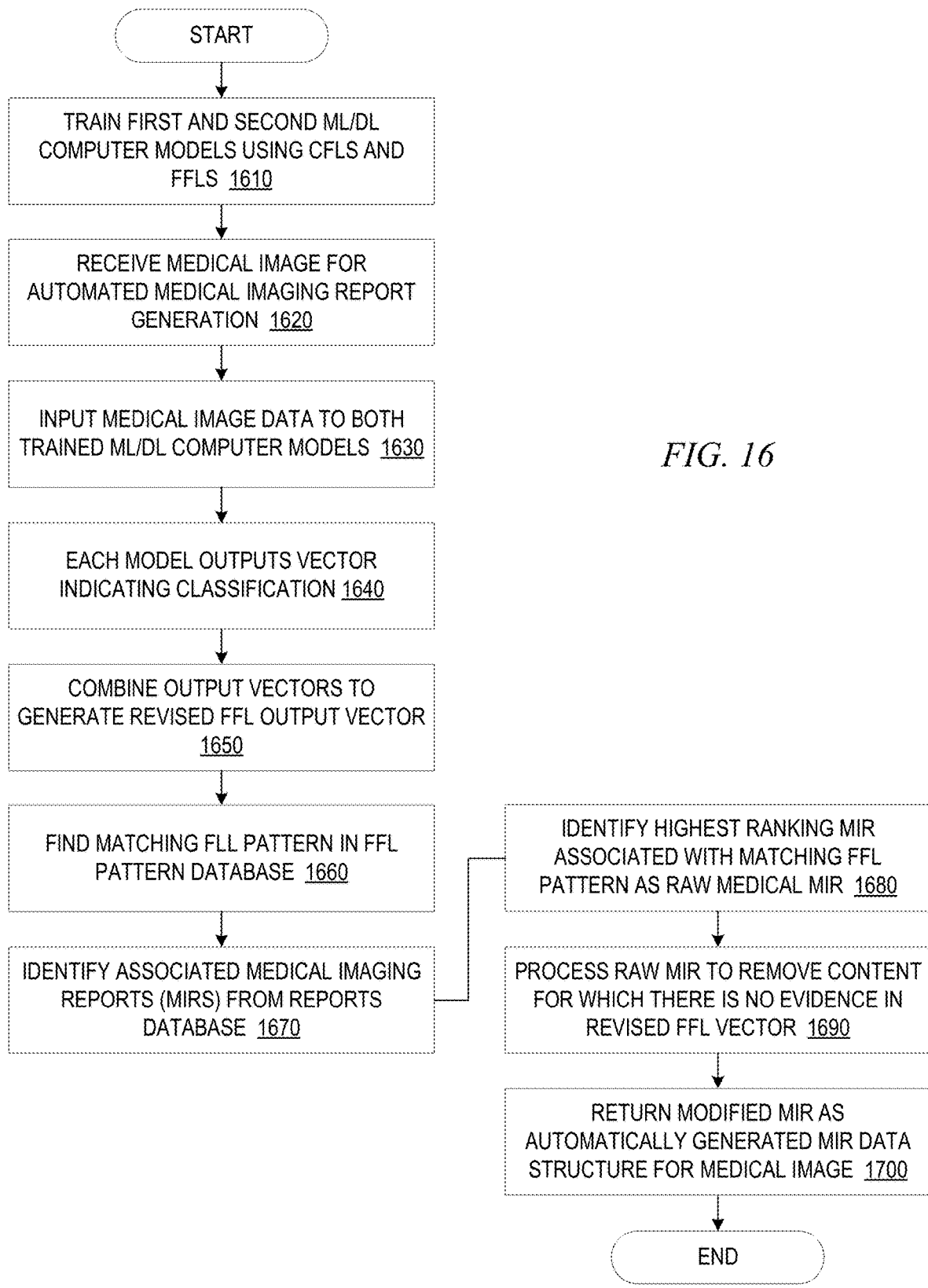
FIG. 16 is flowchart outlining an example operation for automated medical imaging report generation in accordance with one illustrative embodiment.

FIG. 16 is a flowchart outlining an example operation for automated medical imaging report generation in accordance with one illustrative embodiment. The operation outlined in FIG. 16 may be performed by one or more computing devices of one or more data processing systems that are specifically configured to perform the workflow outlined in FIG. 14 above.

As shown in FIG. 16, the operation starts by training a first and second ML/DL computer model based on core finding labels (CFLs) and fine-grained finding labels (FFLs) to thereby generate a pair of trained ML/DL computer models (step 1610). In one illustrative embodiments, the ML/DL computer models may be instances of the ML/DL computer model described previously with regard to FIG. 10, where one instance is trained using CFLs and another instance is trained using FFLs. The FFLs used as a basis for the training of one of these instances may be FFLs defined in fine-grained finding descriptor data structures generated through a process as previously described above. Alternatively, in some illustrative embodiments, the FFLs may be curated in a manner similar to the way that core findings are curated in an automated or semi-automated manner for generating the core findings lexicon/vocabulary, as described above. In such an embodiment, the core findings represent findings without modifiers or with a small limited set of core modifiers, whereas the FFLs have a more comprehensive listing of modifiers and further indicate negative/positive indicators of the core finding.

An input medical image is received from a requestor computing device that is requesting that an automated preliminary read of the medical image be performed and a corresponding automatically generated medical imaging report be provided (step 1620). The received input medical image is input to both of the trained ML/DL computer models for processing (step 1630) with each ML/DL computer model outputting an output vector indicating a classification of the medical image with regard to a predetermine set of classes corresponding to core findings for the first ML/DL computer model, and fine grained findings for the second ML/DL computer model (step 1640). Thus, the CFL trained ML/DL computer model (first ML/DL computer model) outputs a CFL bit vector and the FFL trained ML/DL computer model (second ML/DL computer model) outputs a FFL bit vector.

The output vectors are combined by a fusion module to generate a revised FFL output vector (step 1650) which is provided as input to an FFL pattern and report retrieval engine. The FFL pattern and report retrieval engine searches an FFL pattern database, such as the fine-grained finding descriptor database, to find a matching FFL pattern (step 1660) and identify the associated medical imaging reports from a reports database (step 1670). The FFL pattern and report retrieval engine identifies a highest ranking medical imaging report associated with the matching FFL pattern as a raw medical imaging report for the input medical image data (step 1680). The raw medical imaging report is then processed to remove sentences in the medical imaging report for which there is no evidence in the revised FFL vector (step 1690). The resulting modified medical imaging report is then returned as the automatically generated medical imaging report data structure for the input medical image data (step 1700). The operation then terminates.

Thus, in these further illustrative embodiments, mechanisms are provided for automatically performing preliminary reads of medical images and automatically generating corresponding medical image reports for use by medical practitioners. These mechanisms greatly improve automated computer based medical image analysis and automated computer based medical image report generation as well as medical practice by providing mechanisms to expedite clinical workflows, improve accuracy of clinical workflows, and improve operational efficiencies.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system specifically configured to implement an automated medical imaging report generator, the method comprising:
receiving, by the automated medical imaging report generator, an input medical image data structure specifying a set of image features extracted from an input medical image;
inputting, by the automated medical imaging report generator, the input medical image data structure into at least one trained machine learning computer model trained to predict finding labels based on patterns of image features extracted from medical images;
generating, by the at least one trained machine learning computer model, a prediction of at least one finding label applicable to the input medical image based on processing the set of image features specified in the input medical image data structure and generating a finding label prediction output vector indicating one or more finding labels in a set of predefined finding labels that apply to the input medical image;
performing, by the automated medical imaging report generator, based on the finding label prediction output vector, a lookup operation in a medical report database of previously processed medical imaging report data structures, to find a matching medical imaging report data structure corresponding to the finding label; and
automatically generating, by the automated medical imaging report generator, an output medical imaging report for the input medical image based on natural language content of the matching medical imaging report data structure.

2. The method of claim 1, wherein automatically generating the output medical imaging report for the input medical image comprises:
selecting first natural language content of the matching medical imaging report data structure that comprises evidential support for the at least one finding label;
removing second natural language content of the matching medical imaging report data structure that does not provide evidential support for the at least one finding label; and
generating the output medical imaging report at least by composing the output medical imaging report to have natural language content matching the first natural language content.

3. The method of claim 1, wherein the at least one trained machine learning computer model comprises a first machine learning computer model trained to predict core finding labels (CFLs) based on the patterns of image features extracted from medical images, and a second machine learning computer model trained to predict fine grained finding labels (FFLs) based on the patterns of image features extracted from medical images.

4. The method of claim 3, wherein the first machine learning computer model outputs a first output vector indicating CFLs applicable to the input medical image, and the second machine learning computer outputs a second output vector indicating FFLs applicable to the input medical image, and wherein the first output vector and second output vector are consolidated by a consolidation component to generate a consolidated finding pattern output vector having a vector slot for each unique finding in the CFLs and FFLs.

5. The method of claim 4, wherein the lookup operation is performed based on the consolidated finding pattern output vector, and wherein the matching medical imaging report data structure is analyzed using natural language processing to identify portions of the matching medical imaging report that provide evidential support for findings in a vector slot of the consolidated finding pattern output vector.

6. The method of claim 1, further comprising generating, by a medical imaging report database generator executing in the data processing system, the medical report database at least by:
training a fine grained finding label (FFL) machine learning computer model trained to predict fine grained finding labels (FFLs) applicable to image features extracted from medical images;
processing, by the trained FFL machine learning computer model, a plurality of medical images to output a FFL pattern vector, for each medical image in the plurality of medical images, predicting one or more FFLs applicable to the medical image;
for each medical image in the plurality of medical images, having a same FFL pattern vector, ranking medical imaging reports associated with the plurality of medical images to identify a highest ranking medical imaging report for the FFL pattern vector; and
storing, in the medical report database, the highest ranking medical imaging report in association with the FFL pattern vector.

7. The method of claim 6, wherein ranking the medical imaging reports comprises:
calculating a rank value, for each medical imaging report having the same FFL pattern vector, and for each constituent portion of natural language content in medical imaging reports that provide a portion of an FFL indicated in the FFL pattern vector, a function of a number of medical imaging reports that contain the constituent portion of natural language content; and
ranking the medical imaging reports relative to each other based on their corresponding rank values.

8. The method of claim 1, wherein the at least one trained machine learning computer model comprises a fine grained finding label (FFL) trained machine learning model that predicts FFLs applicable to an input medical image based on features extracted from the input medical image, and wherein the FLLs associate core findings with one or more modifiers defining a sub-type of the core findings.

9. The method of claim 8, wherein the FFL trained machine learning model is trained based on a fine-grained finding descriptor database comprising a plurality of FFL descriptor data structures, wherein the set of FFL descriptor data structures comprise data portions specifying a value of a core finding which corresponds to a core finding instance in a medical imaging report associated with a medical image, one or more modifiers of the core finding, a finding type indicating a type of the core finding modified by the one or more modifiers, and a negativity indicator indicating whether or not the core finding modified by the one or more modifiers is negatively indicated in the medical imaging report associated with the medical image.

10. The method of claim 8, wherein the fine-grained finding descriptor database are generated at least by:
processing, by a fine-grained finding descriptor generation computing tool, medical report natural language content of at least one medical imaging report data structure associated with at least one medical image, based on a core finding lexicon data structure, to extract a set of core finding instances of one or more core findings in the core finding lexicon data structure, from the medical report natural language content, wherein the one or more core findings are terms describing one of anatomical structures or abnormalities present in the at least one medical image;

executing, by the fine-grained finding descriptor generation computing tool, for each core finding instance in the extracted set of core finding instances, automated computer natural language processing operations comprising:

generating a parse tree data structure for a corresponding portion of the medical report natural language content corresponding to the core finding instance;

automatically executing phrasal grouping computer operations on the parse tree data structure to thereby associate one or more modifiers of core findings specified in the portion of the medical report natural language content with the core finding instance, wherein the one or more modifiers are terms further defining a characteristic of the core finding; and generating, by the fine-grained finding descriptor generation computing tool, a FFL descriptor data structure for the core finding instance based on the association of one or more modifiers of the core finding with the core finding instance; and storing the FFL descriptor data structure in the fine-grained finding descriptor database.

11. A computer readable storage medium having a computer readable program stored therein, wherein the computer readable program, when executed on a computing device, causes the computing device to implement an automated medical imaging report generator that automatically generates medical imaging reports at least by:

receiving, by the automated medical imaging report generator, an input medical image data structure specifying a set of image features extracted from an input medical image;

inputting, by the automated medical imaging report generator, the input medical image data structure into at least one trained machine learning computer model trained to predict finding labels based on patterns of image features extracted from medical images;

generating, by the at least one trained machine learning computer model, a prediction of at least one finding label applicable to the input medical image based on processing the set of image features specified in the input medical image data structure and generating a finding label prediction output vector indicating one or more finding labels in a set of predefined finding labels that apply to the input medical image;

performing, by the automated medical imaging report generator, based on the finding label prediction output vector, a lookup operation in a medical report database of previously processed medical imaging report data structures, to find a matching medical imaging report data structure corresponding to the finding label; and automatically generating, by the automated medical imaging report generator, an output medical imaging report for the input medical image based on natural language content of the matching medical imaging report data structure.

12. The computer readable storage medium of claim 11, wherein automatically generating the output medical imaging report for the input medical image comprises:

selecting first natural language content of the matching medical imaging report data structure that comprises evidential support for the at least one finding label;

removing second natural language content of the matching medical imaging report data structure that does not provide evidential support for the at least one finding label; and generating the output medical imaging report at least by composing the output medical imaging report to have natural language content matching the first natural language content.

13. The computer readable storage medium of claim 11, wherein the at least one trained machine learning computer model comprises a first machine learning computer model trained to predict core finding labels (CFLs) based on the patterns of image features extracted from medical images, and a second machine learning computer model trained to predict fine grained finding labels (FFLs) based on the patterns of image features extracted from medical images.

14. The computer readable storage medium of claim 13, wherein the first machine learning computer model outputs a first output vector indicating CFLs applicable to the input medical image, and the second machine learning computer outputs a second output vector indicating FFLs applicable to the input medical image, and wherein the first output vector and second output vector are consolidated by a consolidation component to generate a consolidated finding pattern output vector having a vector slot for each unique finding in the CFLs and FFLs.

15. The computer readable storage medium of claim 14, wherein the lookup operation is performed based on the consolidated finding pattern output vector, and wherein the matching medical imaging report data structure is analyzed using natural language processing to identify portions of the matching medical imaging report that provide evidential support for findings in a vector slot of the consolidated finding pattern output vector.

16. The computer readable storage medium of claim 11, further comprising generating, by a medical imaging report database generator executing in the data processing system, the medical report database at least by:

training a fine grained finding label (FFL) machine learning computer model trained to predict fine grained finding labels (FFLs) applicable to image features extracted from medical images;

processing, by the trained FFL machine learning computer model, a plurality of medical images to output a FFL pattern vector, for each medical image in the plurality of medical images, predicting one or more FFLs applicable to the medical image;

for each medical image in the plurality of medical images, having a same FFL pattern vector, ranking medical imaging reports associated with the plurality of medical images to identify a highest ranking medical imaging report for the FFL pattern vector; and storing, in the medical report database, the highest ranking medical imaging report in association with the FFL pattern vector.

17. The computer readable storage medium of claim 16, wherein ranking the medical imaging reports comprises:

calculating a rank value, for each medical imaging report having the same FFL pattern vector, and for each constituent portion of natural language content in medical imaging reports that provide a portion of an FFL indicated in the FFL pattern vector, a function of a number of medical imaging reports that contain the constituent portion of natural language content; and ranking the medical imaging reports relative to each other based on their corresponding rank values.

18. The computer readable storage medium of claim 11, wherein the at least one trained machine learning computer model comprises a fine grained finding label (FFL) trained machine learning model that predicts FFLs applicable to an input medical image based on features extracted from the input medical image, and wherein the FLLs associate core findings with one or more modifiers defining a sub-type of the core findings.

19. The computer readable storage medium of claim 18, wherein the FFL trained machine learning model is trained based on a fine-grained finding descriptor database comprising a plurality of FFL descriptor data structures, wherein the set of FFL descriptor data structures comprise data portions specifying a value of a core finding which corresponds to a core finding instance in a medical imaging report associated with a medical image, one or more modifiers of the core finding, a finding type indicating a type of the core finding modified by the one or more modifiers, and a negativity indicator indicating whether or not the core finding modified by the one or more modifiers is negatively indicated in the medical imaging report associated with the medical image.

20. An apparatus comprising:
a processor; and
a memory coupled to the processor, wherein the memory comprises instructions which, when executed by the processor, cause the processor to implement an automated medical imaging report generator that automatically generates medical imaging reports at least by:

receiving, by the automated medical imaging report generator, an input medical image data structure specifying a set of image features extracted from an input medical image;

inputting, by the automated medical imaging report generator, the input medical image data structure into at least one trained machine learning computer model trained to predict finding labels based on patterns of image features extracted from medical images;

generating, by the at least one trained machine learning computer model, a prediction of at least one finding label applicable to the input medical image based on processing the set of image features specified in the input medical image data structure and generating a finding label prediction output vector indicating one or more finding labels in a set of predefined finding labels that apply to the input medical image;

performing, by the automated medical imaging report generator, based on the finding label prediction output vector, a lookup operation in a medical report database of previously processed medical imaging report data structures, to find a matching medical imaging report data structure corresponding to the finding label; and automatically generating, by the automated medical imaging report generator, an output medical imaging report for the input medical image based on natural language content of the matching medical imaging report data structure.

* * * * *